US007641906B2

(12) United States Patent
Gu

(10) Patent No.: US 7,641,906 B2
(45) Date of Patent: Jan. 5, 2010

(54) **INTRANASAL IMMUNIZATION WITH DETOXIFIED LIPOOLIGOSACCHARIDE FROM NONTYPEABLE *HAEMOPHILUS INFLUENZAE* OR *MORAXELLA CATARRHALIS***

(75) Inventor: Xin-Xing Gu, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 352 days.

(21) Appl. No.: 11/260,773

(22) Filed: Oct. 27, 2005

(65) Prior Publication Data

US 2006/0062741 A1 Mar. 23, 2006

Related U.S. Application Data

(60) Division of application No. 10/688,115, filed on Oct. 17, 2003, now abandoned, which is a continuation of application No. PCT/US01/32331, filed on Oct. 16, 2001, and a continuation-in-part of application No. 09/789,017, filed on Feb. 20, 2001, now Pat. No. 6,607,725, which is a continuation of application No. PCT/US99/00590, filed on Jan. 12, 1999, said application No. PCT/US01/32331 is a continuation-in-part of application No. 09/610,034, filed on Jul. 5, 2000, now Pat. No. 6,685,949, which is a division of application No. 08/842,409, filed on Apr. 23, 1997, now Pat. No. 6,207,157.

(60) Provisional application No. 60/288,695, filed on May 3, 2001, provisional application No. 60/016,020, filed on Apr. 23, 1996, provisional application No. 60/071,483, filed on Jan. 13, 1998.

(51) Int. Cl.
  *A61K 39/38* (2006.01)
  *A61K 39/02* (2006.01)
  *A61K 45/00* (2006.01)
  *A61K 39/108* (2006.01)

(52) U.S. Cl. .............. 424/184.1; 424/256.1; 424/278.1; 424/251.1

(58) Field of Classification Search .............. 424/184.1, 424/256.1, 278.1, 251.1
See application file for complete search history.

(56) References Cited

U.S. PATENT DOCUMENTS

| H257 H | 4/1987 | Barditch |
|---|---|---|
| 5,601,831 A | 2/1997 | Green et al. |
| 5,607,846 A | 3/1997 | Murphy et al. |
| 5,770,213 A | 6/1998 | Zlotnick |
| 5,948,412 A | 9/1999 | Murphy |
| 5,955,580 A | 9/1999 | Green et al. |
| 6,029,657 A | 2/2000 | Century |
| 6,041,775 A | 3/2000 | Century |
| 6,207,157 B1 | 3/2001 | Gu et al. |

FOREIGN PATENT DOCUMENTS

WO  WO 99/36086  7/1999

OTHER PUBLICATIONS

Boslego et al. (Gonorrhea Vaccines, Chapter 17, 211-223).*
Ellis (New Technologies for Making Vaccines, Text book, 1998; 568-575).*
Asanuma, H. et al. "Isolation and characterization of mouse nasal-associated lymphoid tissue." *J. Immunol. Methods* 202 (1997), pp. 123-131.
Barenkamp S.J. et al. "Development of serum bactericidal activity following nontypable *Haemophilus influenzae* acute otitis media." *Pediatr. Infect. Dis. J.* 9 (1990), pp. 333-339.
Bergquist, C. et al. "Antibody responses in serum and lung to intranasal immunization with *Haemophilus influenzae* type b polysaccharide conjugated to cholera toxin B subuit and tetanus toxoid." *Apmis* 106 (1998), pp. 800-806.
Berman, S. "Otitis media in children". *New Engl. J. Med.* 332 (1995), pp. 1560-1565.
Bernstein, J.M. et al. "Micro-ecology of the nasopharyngeal bacterial flora in otitis-prone and non-otitis-prone children." *Acta Otolaryngol.* 113 (1993), pp. 88-92.
Brook, I. et al. "Microbiologic characteristics of persistent otitis media." *Arch. Otolaryngol. Head Neck Surg.* 124 (1998), pp. 1350-1352.
Campagnari, A.A. et al. "Antigenic diversity of lipooligosaccharides of nontypable *Haemophilus influenzae.*" *Infect. Immun.* 55 (1987), pp. 882-887.
Commisso, R. et al. "Acute otitis media: bacteriology and bacterial resistance in 205 pediatric patients." *Int. J. Pediatr. Otorhinolaryngol.* 56 (2000), pp. 23-31.
Cripps, A.W. et al. "Respiratory immunity stimulated by intestinal immunization with purified nontypeable *Haemophilus influenzae* antigens." *J. Infect. Dis.* 165 (1992), pp. S199-S201.
Demaria, T.F. et al. "Evaluation of the virulence of nontypeable *Haemophilus influenzae* lipooligosaccharide htrB and rfaD mutants in the chinchilla model of otitis media." *Infect. Immun.* 65 (1997), pp. 4431-4435.
Faden, H. et al. "Relationship between nasopharyngeal colonization and the development of otitis media in children." *J. Infect. Dis.* 175 (1997), pp. 1440-1445.
Gu, X.X. et al. "Production and characterization of monoclonal antibodies to type 8 lipooligosaccharide of *Neisseria meningitidis.*" *J. Clin. Microbiol.* 30 (1992), pp. 2047-2053.
Gu, X.X. et al. "Quantitation and biological properties of released and cell-bound lipooligosaccharides from nontypeable *Haemophilus influenzae.*" *Infect. Immun.* 63 (1995), pp. 4115-4120.
Gu, X.X. et al. "Synthesis, characterization, and immunologic properties of detoxified lipooligosaccharide from nontypeable *Haemophilus influenzae* conjugated to proteins." *Infect. Immun.* 64 (1996), pp. 4047-4053.

(Continued)

*Primary Examiner*—Robert B Mondesi
*Assistant Examiner*—Lakia J Tongue
(74) *Attorney, Agent, or Firm*—Edwards Angell Palmer & Dodge LLP; Peter F. Corless

(57) ABSTRACT

The invention relates to intranasal immunization with detoxified lipooligosaccharide from nontypeable *Haemophilus influenzae* or *Moraxella catarrhalis*.

25 Claims, 19 Drawing Sheets

OTHER PUBLICATIONS

Gu, X.X. et al. "Detoxified lipooligosaccharide from nontypeable *Haemophilus influenzae* conjugated to proteins confers protection against otitis media in chinchillas." *Infect. Immun.* 65 (1997), pp. 4488-4493.

Gu, X.X. et al. "Development of a vaccine to prevent Otitis media caused by *Nontypeable Haemophilus influenzae*" The 4th Extraordinary International Symposium on Recent Advances in Otitis Media, endai, Japan, Apr. 16-20, 2001, Abstract 72, p. 116.

Hirano, T. et al. "Intranasal immunization with a lipooligosaccharide-based conjugate vaccine from nontypeable *Haemophilus influenzae* enhances bacterial clearance in mouse nasopharynx." *FEMS Immunol. Med. Microbiol.* 35; (2003), pp. 1-10.

Hotomi, M. et al. "Specific mucosal immunity and enhanced nasopharyngeal clearance of nontypeable *Haemophilus influenzae* after intranasal immunization with outer membrane protein P6 and cholera toxin." *Vaccine* 16 (1998), pp. 1950-1956.

Jakobsen, H. et al. "Intranasal immunization with pneumococcal polysaccharide conjugate vaccines protects mice against invasive pneumococcal infections." *Infect. Immun.* 67 (1999), pp. 4128-4133.

Kauppi-Korkeila, M. et al. "Mechanism of antibody-mediated reduction of nasopharyngeal colonization by *Haemophilus influenzae* type b studied in an infant rat model." *J. Infect. Dis.* 174 (1996), pp. 1337-1340.

Kodama, S. et al. "Induction of specific immunoglobulin A and Th2 immune responses to P6 outer membrane protein on nontypeable *Haemophilus influenzae* in middle ear mucosa by intranasal immunization." *Infect. Immun.* 68 (2000), pp. 2294-2300.

Kurono, Y. et al. "Effects of oral and systemic immunization on nasopharyngeal clearance of nontypeable *Haemophilus influenzae* in BALB/c mice." *Laryngoscope* 106 (1996), pp. 614-618.

Kurono, Y. et al. "Nasal immunization induces *Haemophilus influenzae*-specific Th1 and Th2 responses with mucosal IgA and systemic IgG antibodies for protective immunity." *J. Infect. Dis.* 180 (1999), pp. 122-132.

Kyd, J.M. et al. "Enhanced respiratory clearance of nontypeable *Haemophilus influenzae* following mucosal immunization with P6 in a rat model." *Infect. Immun.* 63 (1995), pp. 2931-2940.

Kyd, J..M. et al. "Potential of a novel protein, OMP26, from nontypeable *Haemophilus influenzae* to enhance pulmonary clearance in a rat model." *Infect. Immun.* 66 (1998), pp. 2272-2278.

Mansson, M. et al. "A new structural type for *Haemophilus influenzae* lipopolysaccharide. Structural analysis of the lipopolysaccharide from nontypeable *Haemophilus influenzae* strain 486." *Eur. J. Biochem.* 268 (2001), pp. 2148-2159.

Mansson, M. et al. "Structural analysis of the lipopolysaccharide from nontypeable *Haemophilus influenzae* strain 1003." *Eur. J. Biochem.* 269 (2002), pp. 808-818.

McGehee, J.L. et al. "Effect of primary immunization on pulmonary clearance of nontypable *Haemophilus influenzae.*" *Am. J. Respir. Cell. Mol. Biol.* 1 (1989), pp. 201-210.

Murphy, T.F. et al. "Outer membrane protein and lipooligosaccharide analysis of paired nasopharyngeal and middle ear isolates in otitis media due to nontypable *Haemophilus influenzae*: pathogenetic and epidemiological observations". *J. Infect. Dis.* 156 (1987), pp. 723-731.

Neuberger M.S. et al. "Activation of mouse complement by monoclonal mouse antibodies." *Eur. J. Immunol.* 11 (1981), pp. 1012-1016.

Ogra, P.L. et al. "Characteristics of secretory immune system in human middle ear: implications in otitis media." *J. Immunol.* 112 (1974), pp. 488-495.

Patrick, C.C. et al. "Antigenic characterization of the oligosaccharide portion of the lipooligosaccharide of nontypable *Haemophilus influenzae.*" *Infect. Immun.* 55 (1987), pp. 2902-2911.

Phillips, N.J. et al. "Structural characterization of the cell surface lipooligosaccharides from a nontypable strain of *Haemophilus influenzae.*" *Biochemistry* 31 (1992), pp. 4515-4526.

Rahman, M.M. et al. "The structural heterogeneity of the lipooligosaccharide (LOS) expressed by pathogenic non-typeable *Haemophilus influenzae* strain NTHi 9274." *Glycobiology* 9 (1999), pp. 1371-1380.

Sabirov, A. et al. "Intranasal immunization enhances clearance of nontypeable *Haemophilus influenzae* and reduces stimulation of tumor necrosis factor alpha production in the murine model of otitis media." *Infect. Immun.* 69 (2001), pp. 2964-2971.

Schweda, E.K. et al. "Structural analysis of lipopolysaccharide oligosaccharide epitopes expressed by non-typeable *Haemophilus influenzae* strain 176." *Carbohydr. Res.* 337 (2002), pp. 409-420.

Shen, X. et al. "Systemic and mucosal immune responses in mice after mucosal immunization with group B streptococcus type III capsular polysaccharide-cholera toxin B subunit conjugate vaccine." *Infect. Immun.* 68 (2000), pp. 5749-5755.

Shurin, P.A. et al. "Bactericidal antibody and susceptibility to otitis media cause by nontypeable strains of *Haemophilus influenzae.*" *J. Pediatr.* 97 (1980), pp. 364-369.

Sloyer, J.L. Jr., et al. "Immune response to acute otitis media: association between middle ear fluid antibody and the clearing of clinical infection." *J. Clin. Microbiol.* 4 (1976), pp. 306-308.

Sun, J. et al. "Biological activities of antibodies elicited by lipooligosaccharide based-conjugate vaccines of nontypeable *Haemophilus influenzae* in an otitis media model." *Vaccine* 18 (2000), pp. 1264-1272.

Swords, W.E. et al. "Nontypeable *Haemophilus influenzae* adhere to and invade human bronchial epithelial cells via an interaction of lipooligosaccharide with the PAF receptor." *Mol. Microbiol.* 37 (2000), pp. 13-27.

Ueyama, T. et al. "Identification of common lipooligosaccharide types in isolates from patients with otitis media by monoclonal antibodies against nontypeable *Haemophilus influenzae* 9274." *Clin. Diagn. Lab. Immunol.* 6 (1999), pp. 96-100.

Vogel, L. et al. "Opsono-phagocytosis of non-encapsulated *Haemophilus influenzae.*" *Adv. Exp. Med. Biol.* 371A (1995), pp. 695-698.

Wagner, D.K. et al. "Analysis of immunoglobulin G antibody responses after administration of live and inactivated influenza A vaccine indicates that nasal wash immunoglobulin G is a transudate from sreum." *J. Clin. Microbiol.* 25 (1987), pp. 559-562.

Williams, R.C. et al. "Inhibition of bacterial adherence by secretory immunoglobulin A: a mechanism of antigen disposal." *Science* 177 (1972), pp. 697-699.

Wu, T.H. et al. "Outer membrane proteins as a carrier for detoxified lipooligosaccharide conjugate vaccines for nontypeable *Haemophilus influenzae.*" *Infect. Immun.* 67 (1999), pp. 5508-5513.

*Stedman's Medical Dictionary*, (27th ed., 2000) p. 1555.

* cited by examiner

INTRANASAL IMMUNIZATION WITH DETOXIFIED LIPOOLIGOSACCHARIDE FROM NONTYPEABLE *HAEMOPHILUS INFLUENZAE* OR *MORAXELLA CATARRHALIS*

RELATED APPLICATIONS

This application is a divisional of U.S. patent application Ser. No. 10/688,115, filed Oct. 17, 2003 now abandoned, which is continuation and claims the benefit of priority of International Application No. PCT/US01/32331 filed Oct. 16, 2001, designating the United States of America and published in English, which claims the benefit of priority of U.S. Provisional Application No. 60/288,695 filed May 3, 2001, and for U.S. purposes only, PCT/US01/32331 is a continuation-in-part of U.S. patent application Ser. No. 09/789,017 filed Feb. 20, 2001, issued as U.S. Pat. No. 6,607,725, which is a divisional of U.S. patent application Ser. No. 08/842,409 filed Apr. 23, 1997, issued as U.S. Pat. No. 6,207,157, which claims the benefit of priority of U.S. Pat. Appl. No. 60/016,020 filed Apr. 23, 1996, and PCT/US01/32331 is also a continuation-in-part of U.S. patent application Ser. No. 09/610,034 filed Jul. 5, 2000, issued as U.S. Pat. No. 6,685,949, which is a continuation of Intl. Pat. Appl. No. PCT/US99/00590 filed Jan. 12, 1999, designating the United States of America and published in English, which claims the benefit of priority of U.S. Pat. Appl. No. 60/071,483 filed Jan. 13, 1998; the disclosures of such related applications are incorporated herein by reference in their entireties.

FIELD OF THE INVENTION

The invention relates to intranasal immunization with detoxified lipooligosaccharide from nontypeable *Haemophilus influenzae* or *Moraxella catarrhalis*.

BACKGROUND OF THE INVENTION

Nontypeable *Haemophilus influenzae* (NTHi) is an important cause of otitis media (OM) in children and respiratory tract diseases in adults (Klein, J. O. et al. 1992 *Adv Pediatr* 39:127-156; Murphy, T. F. et al. 1987 *Rev Infect Dis* 9:1-15; Musher, D. M. et al. 1983 *Ann Intern Med* 99:344-350). *Moraxella (Branhamella) catarrhalis* (Catlin, B. W. 1990 *Clin Microbiol Rev* 3:293-320; Doern, G. V. 1986 *Diagn Microbiol Infect Dis* 4:191-201; Enright, M. C., and H. McKenzie 1997 *J Med Microbiol* 46:360-371) is recognized as the third-most-common pathogen causing otitis media and sinusitis in children, after *Streptococcus pneumoniae* and nontypeable *Haemophilus influenzae* (Bluestone, C. D. 1986 *Drugs* 31(Suppl. 3): 132-141; Faden, H. et al. 1994 *J Infect Dis* 169:1312-1317). This gram-negative *diplococcus* is also a cause of respiratory tract infections in adults (Boyle, F. M. et al. 1991 *Med J Aust* 154:592-596; Sarubbi, F. A. et al. 1990 *Am J Med* 88:9S-14S), especially those with chronic obstructive pulmonary diseases (Nicotra, B. et al. 1986 *Arch Intern Med* 146:890-893) or compromised immune systems (Alaeus, A. and G. Stiemstedt *Scand J Infect Dis* 23:115-116; Enright, M. C. and H. McKenzie. 1997 *J Med Microbiol* 46:360-371).

Nontypeable *Haemophilus influenzae* (NTHi) is an important cause of otitis media in children and of pneumonitis in adults with depressed resistance. Lipooligosaccharide (LOS) is a major surface antigen of NTHi and elicits bactericidal and opsonic antibodies. Gu, X. X. et al. 1996 *Infect Immun* 64:4047-4053 prepared detoxified LOS (dLOS) protein conjugates from NTHi for use as experimental vaccines. LOS from NTHi 9274 was treated with anhydrous hydrazine and had its toxicity reduced to clinically acceptable levels. Hydrazine treatment of NTHi LOS resulted in a 10,000-fold reduction in the level of "endotoxin", which is at clinically acceptable levels (W.H.O. Expert Committee on Biological Standardization 1991 *W.H.O. Tech Rep Ser* 814:15-37). dLOS was bound to tetanus toxoid (TT) or high-molecular-weight proteins (HMPs) from NTHi through a linker of adipic acid dihydrazide to form dLOS-TT or dLOS-HMP. The molar ratio of the dLOS to protein carriers ranged from 26:1 to 50:1. The antigenicity of the conjugates was similar to that of the LOS alone as determined by double immunodiffusion. Subcutaneous or intramuscular injection of the conjugates elicited a 28- to 486-fold rise in the level of immunoglobulin G antibodies in mice to the homologous LOS after two or three injections and a 169- to 243-fold rise in the level of immunoglobulin G antibodies in rabbits after two injections. The immunogenicity of the conjugates in mice and rabbits was enhanced by formulation with monophosphoryl lipid A plus trehalose dimycolate. In rabbits, conjugate-induced LOS antibodies induced complement-mediated bactericidal activity against the homologous strain 9274 and prototype strain 3189. These results indicate that a detoxified LOS-protein conjugate is a candidate vaccine for otitis media and pneumonitis caused by NTHi. Gu, X. X. et al. 1997 *Infect Immun* 65:4488-4493 determined that subcutaneous or intramuscular injections of detoxified-lipooligosaccharide (dLOS)-protein conjugates from NTHi protected against otitis media in chinchillas.

*Moraxella (Branhamella) catarrhalis* (*M. catarrhalis*) is an important cause of otitis media and sinusitis in children and of lower respiratory tract infections in adults. Lipooligosaccharide (LOS) is a major surface antigen of the bacterium and elicits bactericidal antibodies. Treatment of the LOS from strain ATCC 25238 with anhydrous hydrazine reduced its toxicity 20,000-fold, as assayed in the *Limulus amebocyte* lysate (LAL) test. The detoxified LOS (dLOS) was coupled to tetanus toxoid (TT) or high-molecular-weight proteins (HMP) from nontypeable *Haemophilus influenzae* through a linker of adipic acid dihydrazide to form dLOS-TT or dLOS-HMP. The molar ratios of dLOS to TT and HMP conjugates were 19:1 and 31:1, respectively. The antigenicity of the two conjugates was similar to that of the LOS, as determined by double immunodiffusion. Subcutaneous or intramuscular injection of both conjugates elicited a 50- to 100-fold rise in the geometric mean of immunoglobulin G (IgG) to the homologous LOS in mice after three injections and a 350- to 700-fold rise of anti-LOS IgG in rabbits after two injections. The immunogenicity of the conjugate was enhanced by formulation with monophosphoryl lipid A plus trehalose dimycolate. In rabbits, conjugate-induced antisera had complement-mediated bactericidal activity against the homologous strain and heterologous strains of *M. catarrhalis*. These results indicate that a detoxified LOS-protein conjugate is a candidate for immunization against *M. catarrhalis* diseases.

Current pediatric immunization programs include too many injections in the first months of life. Oral or nasal vaccine delivery eliminates the requirement for needles. There is a need for mucosal vaccines against NTHi- and *M. catarrhalis*-caused otitis media in children and other NTHi- and *M. catarrhalis*-caused diseases in children and adults.

SUMMARY OF THE INVENTION

The invention relates to intranasal immunization with detoxified lipooligosaccharide from nontypeable *Haemophilus influenzae* or *Moraxella catarrhalis*.

DETAILED DESCRIPTION OF THE INVENTION

Figure 1:
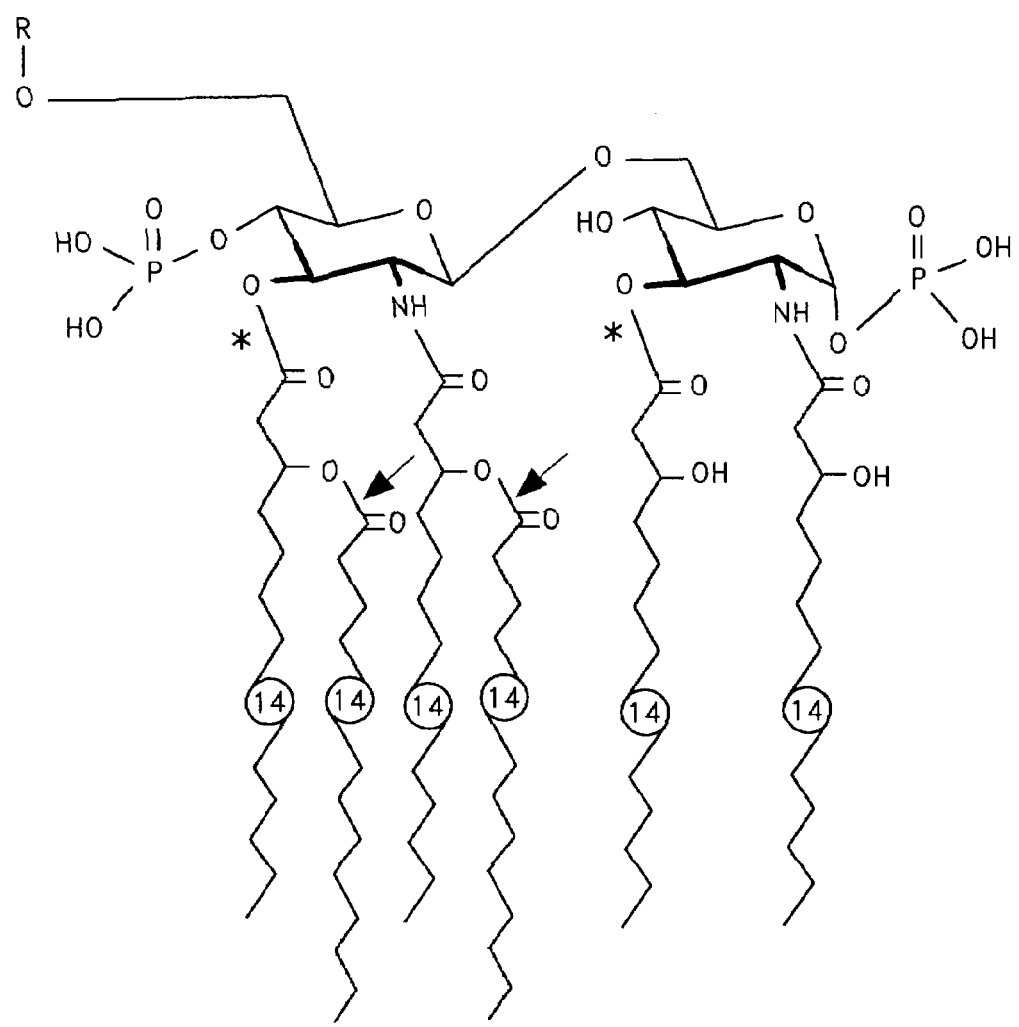
FIG. 1 shows the proposed chemical structure of lipid A from nontypeable *Haemophilus influenzae* lipooligosaccharide (LOS). R=site of attachment of the oligosaccharide chain. Hydrazine treatment of LOS removes primary O-linked fatty acids from 3-hydroxy groups of diglucosamine (*) and secondary O-linked fatty acids from hydroxy groups of 3-hydroxy fatty acids of lipid A (arrow).

The invention relates to an immunogenic composition comprising an immunizing amount of Nontypeable *Haemophilus influenzae* (NTHi) or *Moraxella catarrhalis* lipooligosaccharide (LOS) from which at least one primary O-linked fatty acid has been removed to form detoxified LOS (dLOS) and an immunogenic carrier covalently linked thereto, optionally where the dLOS and the immunogenic carrier are covalently linked by a linker, and a mucosal adjuvant or delivery system.

In accordance with the present invention, it has now been surprisingly found that mucosal administration, preferably intranasally, of NTHi or *M. catarrhalis* lipooligosaccharide (LOS) from which at least one primary O-linked fatty acid has been removed to form detoxified LOS (dLOS) and an immunogenic carrier covalently linked thereto, optionally where the dLOS and the immunogenic carrier are covalently linked by a linker, elicits an immunological response and can even inhibit colonization by NTHi or *M. catarrhalis* and prevent otitis media and other respiratory diseases caused by NTHi or *M. catarrhalis* infection.

Accordingly, in one aspect, the present invention provides a method for inducing an immunological response in a host, preferably a human host, to inhibit colonization by NTHi or *M. catarrhalis* or prevent otitis media and other respiratory diseases caused by NTHi or *M. catarrhalis* infection by mucosal administration, preferably intranasal administration, to the host of an effective amount of NTHi or *M. catarrhalis* lipooligosaccharide (LOS) from which at least one primary O-linked fatty acid has been removed to form detoxified LOS (dLOS) and an immunogenic carrier covalently linked thereto, optionally where the dLOS and the immunogenic carrier are covalently linked by a linker, and a mucosal adjuvant or delivery system.

Moreover, in another aspect, the present invention provides use of an effective amount of NTHi or *M. catarrhalis* lipooligosaccharide (LOS) from which at least one primary O-linked fatty acid has been removed to form detoxified LOS (dLOS) and an immunogenic carrier covalently linked thereto, optionally where the dLOS and the immunogenic carrier are covalently linked by a linker, and a mucosal adjuvant or delivery system, for mucosal administration, preferably intranasal administration, to a host, preferably a human host, for inducing an immunological response to inhibit colonization by NTHi or *M. catarrhalis* or prevent otitis media and other respiratory diseases caused by NTHi or *M. catarrhalis* infection.

The present invention relates to a conjugate vaccine comprising nontypeable *Haemophilus influenzae* (NTHi) or *Moraxella catarrhalis* lipooligosaccharide (LOS) from which at least one primary O-linked esterified fatty acid has been removed to form detoxified LOS (dLOS), and an immunogenic carrier covalently linked thereto, optionally where the dLOS and immunogenic carrier are covalently linked by a linker. LOS may be extracted from NTHi or *M. catarrhalis* and purified according to conventional processes. NTHi and *M. catarrhalis* lipooligosaccharides may be of any serotype. As a matter of example, serotypes I, II, III, IV and V for NTHi are cited (Campagnari, A. A. et al. 1987 *Infect Immun* 55:882-887; Partick, C. C. et al. 1987 *Infect Immun* 55:2902-2911), but the LOS used for the conjugates herein was highly cross-reactive to the majority of NTHi clinical isolates. For *M. catarrhalis*, three major LOS serotypes: A, B and C are cited (Vaneechoutte, M. G et al. 1990 *J Clin Microbiol* 28:182-187). One or several lipooligosaccharides may be concomitantly administered by the mucosal route. In particular, the medicament, i.e., the vaccine, for mucosal administration may contain several lipooligosaccharides, each of a particular serotype.

Figure 2:
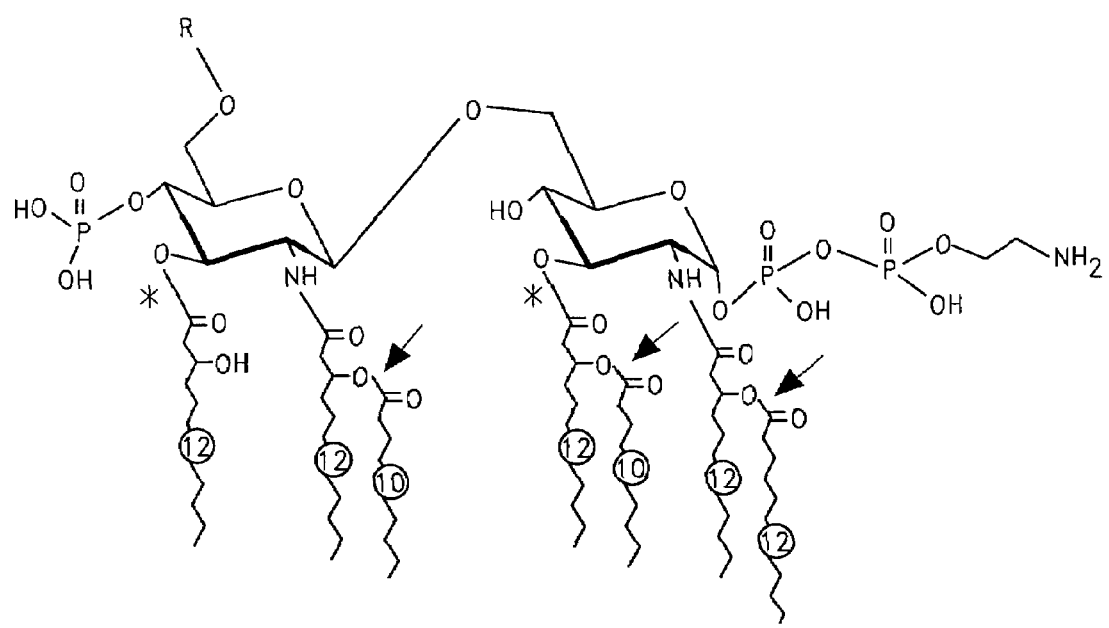
FIG. 2 shows the proposed chemical structure of lipid A from *Moraxella catarrhalis* lipooligosaccharide (LOS). R=site of attachment of the oligosaccharide chain. Hydrazine treatment of LOS removes primary O-linked fatty acids from 3-hydroxy groups of diglucosamine (*) and secondary O-linked fatty acids from hydroxy groups of 3-hydroxy fatty acids of lipid A (arrow).

A proposed chemical structure of lipid A from nontypeable *Haemophilus influenzae* lipooligosaccharide (LOS) is shown in FIG. 1. A proposed chemical structure of lipid A from *Moraxella catarrhalis* lipooligosaccharide (LOS) is shown in FIG. 2. The O-linked esterified fatty acids shown by the asterisks are defined as primary O-linked fatty acids and those shown by the arrows are defined as secondary O-linked fatty acids. The conjugate vaccine may also comprise LOS from which both primary O-linked fatty acids have been removed. In addition to the removal of at least one primary O-linked fatty acid from LOS, one or both of the secondary O-linked fatty acids may also be removed. The number of primary and secondary O-linked fatty acids removed by hydrazine treatment, or by treatment with any other reagent capable of hydrolyzing these linkages, will depend on the time and temperature of the hydrolysis reaction. The determination of the number of fatty acid chains which have been removed during the reaction can be determined by standard analytical methods including mass spectrometry and nuclear magnetic resonance (NMR).

Although the use of hydrazine for detoxification of LOS from NTHi or *M catarrhalis* is described herein, the use of any reagent or enzyme capable of removing at least one primary O-linked fatty acid from LOS is within the scope of the present invention. For example, other bases such as sodium hydroxide, potassium hydroxide, and the like may be used.

After removal of one or more primary O-linked fatty acids, dLOS is optionally conjugated to a linker, such as adipic acid dihydrazide (ADH), prior to conjugation to an immunogenic carrier protein, such as tetanus toxoid (TT). Although ADH is the preferred linker, the use of any linker capable of stably and efficiently conjugating dLOS to an immunogenic carrier protein is contemplated. The use of linkers is well known in the conjugate vaccine field (see Dick et al. *Conjugate Vaccines*, J. M. Cruse and R. E. Lewis, Jr., eds. Karger, New York, pp. 48-114, 1989).

dLOS may be directly covalently bonded to the carrier. This may be accomplished, for example, by using the cross-linking reagent glutaraldehyde. However, in a preferred embodiment, dLOS and the carrier are separated by a linker. The presence of a linker promotes optimum immunogenicity of the conjugate and more efficient coupling of the dLOS with the carrier. Linkers separate the two antigenic components by chains whose length and flexibility can be adjusted as desired. Between the bifunctional sites, the chains can contain a variety of structural features, including heteroatoms and cleavage sites. Linkers also permit corresponding increases in translational and rotational characteristics of the antigens, increasing access of the binding sites to soluble antibodies. Besides ADH, suitable linkers include, for example, heterodifunctional linkers such as $\epsilon$-aminohexanoic acid, chlorohexanol dimethyl acetal, D-glucuronolactone and p-nitrophenyl amine. Coupling reagents contemplated for use in the present invention include hydroxysuccinimides and carbodiimides. Many other linkers and coupling reagents known to those of ordinary skill in the art are also suitable for use in the invention (e.g. cystamine). Such compounds are discussed in detail by Dick et al. (Dick et al. *Conjugate Vaccines*, J. M. Cruse and R. E. Lewis, Jr., eds. Karger, New York, pp. 48-114, 1989).

The presence of a carrier increases the immunogenicity of the dLOS. Polymeric immunogenic carriers can be a natural or synthetic material containing a primary and/or secondary amino group, an azido group or a carboxyl group. The carrier may be water soluble or insoluble.

Any one of a variety of immunogenic carrier proteins may be used in the conjugate vaccine of the present invention. Such classes of proteins include pili, outer membrane proteins and excreted toxins of pathogenic bacteria, nontoxic or "toxoid" forms of such excreted toxins, nontoxic proteins antigenically similar to bacterial toxins (cross-reacting materials or CRMs) and other proteins. Nonlimiting examples of bacterial toxoids contemplated for use in the present invention include tetanus toxin/toxoid, diphtheria toxin/toxoid, detoxified *P. aeruginosa* toxin A, cholera toxin/toxoid, pertussis toxin/toxoid and *Clostridium perfringens* exotoxins/toxoid. The toxoid forms of these bacterial toxins are preferred. The use of viral proteins (i.e. hepatitis B surface/core antigens; rotavirus VP 7 protein and respiratory syncytial virus F and G proteins) is also contemplated.

CRMs include CRM197, antigenically equivalent to diphtheria toxin (Pappenheimer et al. 1972 *Immunochem* 9:891-906) and CRM3201, a genetically manipulated variant of pertussis toxin (Black et al. 1988 *Science* 240:656-659). The use of immunogenic carrier proteins from non-mammalian sources including keyhole limpet hemocyanin, horseshoe crab hemocyanin and plant edestin is also within the scope of the invention.

Outer membrane proteins include high molecular weight proteins (HMPs), P4 and P6 from nontypeable *Haemophilus influenzae* and CD and USPA from *Moraxella catarrhalis*. For a list of other outer membrane proteins, see PCT WO98/53851.

There are many coupling methods which can be envisioned for dLOS-protein conjugates. In the disclosure set forth below, dLOS is selectively activated by 1-ethyl-3-(3-dimethylaminopropyl) carbodiimide (EDC)-mediated ADH derivatization of the terminal 3-deoxy-D-manno-2-octulosonic acid (KDO) group of dLOS, followed by EDC-mediated coupling to TT. Alternatively, another method for producing the instant conjugates involves cystamine derivatization of dLOS, by, for example, EDC-mediated derivatization, followed by disulfide conjugation to N-succimidyl-3-(2-pyridyldithio) propionate-derivatized protein. Other methods well known in the art for effecting conjugation of oligosaccharides to immunogenic carrier proteins are also within the scope of the invention. Such methods are described in, for example, U.S. Pat. Nos. 5,153,312 and 5,204,098; and EP 0 497 525; and EP 0 245 045.

The molar ratio of ADH to dLOS in the reaction mixture is typically between about 10:1 and about 250:1. A molar excess of ADH is used to ensure more efficient coupling and to limit dLOS-dLOS coupling. In a preferred embodiment, the molar ratio is between about 50:1 and about 150:1; in a most preferred embodiment, the molar ratio is about 100:1. Similar ratios of AH-dLOS to both TT and HMP in the reaction mixture are also contemplated. In a preferred embodiment, one ADH per dLOS is present in the AH-dLOS conjugate. In another preferred embodiment, in the final dLOS-carrier protein conjugate, the molar ratio of dLOS to carrier is between about 15 and about 75, preferably between about 25 and about 50.

Immunogenic compositions including vaccines may be prepared as inhalables, sprays and the like (e.g., nasal spray, aerosol spray or pump spray and the like), e.g., as liquid solutions or emulsions, etc. Aerosol spray preparations can be in a pressurized container with a suitable propellant such as a hydrocarbon propellant. Pump spray dispensers can dispense a metered dose or, a dose having a particular particle or droplet size. Pump spray dispensers are commercially available, e.g., from Valois of America, Inc., Connecticut. Nasal spray dispensers are commonly fabricated from a flexible material such as plastic and cause a spray to dispense in response to being squeezed. Anti-inflammatories, such as "Vanceril" are commercially available in oral and nasal aerosol form for mucosal administration; the anti-inflammatory "Vancerase" is commercially available in a pump-spray dispenser for nasal administration; cold remedies such as "Dristan" are commercially available in nasal spray (squeeze) dispensers (so that the reader is aware that aerosol, pump and squeeze dispensers are known and available).

The lipooligosaccharide may be mixed with pharmaceutically acceptable excipients which are compatible therewith. Such excipients may include water, saline, dextrose, glycerol, ethanol, and combinations thereof. The immunogenic compositions and vaccines may further contain auxiliary substances, such as wetting or emulsifying agents, pH buffering agents, or mucosal adjuvants or delivery systems to enhance the effectiveness thereof.

For use in the present invention, the lipooligosaccharide is combined with a mucosal adjuvant or delivery system. See Singh, M. & O'Hagan, D., November 1999 *Nature Biotechnology* 17:1075-1081; and Ryan, E. J. et al. August 2001 *Trends in Biotechnology* 19:293-304. Suitable mucosal adjuvants and delivery systems are listed in the table below.

TABLE

Mucosal Adjuvants and Delivery Systems

Aluminum salts
Chitosan
Cytokines (e.g., IL-1, IL-2, IL-12, IFN-γ, GM-CSF)
Saponins (e.g., QS21)
Muramyl dipeptide (MDP) derivatives
CpG oligos
Lipopolysaccharide (LPS) of gram-negative bacteria
Monophosphoryl Lipid A (MPL)
Polyphosphazenes
Emulsions (e.g., Freund's, SAF, MF59)
Virosomes
Iscoms
Cochleates
Poly(lactide-co-glycolides) (PLG) microparticles
Poloxamer particles
Virus-like particles
Heat-labile enterotoxin (LT), LT B subunit
Cholera toxin (CT), CT B subunit
Mutant toxins (e.g., LTK63 and LTR72)
Microparticles
Liposomes The mucosal administration preferably is effected intranasally, e.g., to the olfactory mucosa, to provide protection to the host against both bacterial colonization and systemic infection. The intranasal administration also may provide protection to the host against pulmonary infection as well as protection to the host against an infection starting as a pulmonary infection. However, the mucosal administration can also involve respiratory mucosa, gingival mucosa or alveolar mucosa. Thus, the administration can be perlingual or sublingual or into the mouth or respiratory tract; but intranasal administration is preferred.

Compositions of the invention, especially for nasal administration, are conveniently provided as isotonic aqueous solutions, suspensions or viscous compositions which may be buffered to a selected pH. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer.

Liquid sprays and drops are normally easier to prepare than gels and other viscous compositions. Additionally, they are somewhat more convenient to administer, especially in multidose situations. Viscous compositions, on the other hand can be formulated within the appropriate viscosity range to provide longer contact periods with mucosa, such as the nasal mucosa.

Suitable nontoxic pharmaceutically acceptable carriers, and especially nasal carriers, will be apparent to those skilled in the art of pharmaceutical and especially nasal pharmaceutical formulations. For those not skilled in the art, reference is made to the text entitled *Remington's Pharmaceutical Sciences*, a reference book in the field. Obviously, the choice of suitable carriers will depend on the exact nature of the particular mucosal dosage form, e.g., nasal dosage form, required [e.g., whether the composition is to be formulated into a solution such as a nasal solution (for use as drops or as a spray), a nasal suspension, a nasal ointment, a nasal gel or another nasal form]. Preferred mucosal and especially nasal dosage forms are solutions, suspensions and gels, which normally contain a major amount of water (preferably purified water) in addition to the antigen (PspA). Minor amounts of other ingredients such as pH adjusters (e.g., a base such as NaOH), emulsifiers or dispersing agents, buffering agents, preservatives, wetting agents and jelling agents (e.g., methylcellulose) may also be present. The mucosal (especially nasal) compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Compositions within the scope of this invention can contain a humectant to inhibit drying of the mucous membrane and to prevent irritation. Any of a variety of pharmaceutically acceptable humectants can be employed including, for example sorbitol, propylene glycol or glycerol. As with the thickeners, the concentration will vary with the selected agent, although the presence or absence of these agents, or their concentration, is not an essential feature of the invention.

Enhanced absorption across the mucosal and especially nasal membrane can be accomplished employing a pharmaceutically acceptable surfactant. Typically useful surfactants for compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration is form 1% to 10% based on the total weight.

A pharmaceutically acceptable preservative can be employed to increase the shelf-life of the compositions. Benzyl alcohol may be suitable, although a variety of preservatives including, for example, Parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the lipooligosaccharide. This will present no problem to those skilled in chemical and pharmaceutical principles, or problems can be readily avoided by reference to standard texts or by simple experiments (not involving undue experimentation), from this disclosure.

The therapeutically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical arts taking into consideration such factors as the age, sex, weight, and condition of the particular patient, and the mucosal route of administration. Dosages for humans or other mammals can be determined without undue experimentation by the skilled artisan from experiments involving mice, rabbits, chinchillas, etc.

The vaccine composition which is administered intranasally as provided herein may be formulated in any convenient manner and in a dosage formulation consistent with the mode of administration and the elicitation of a protective response. The quantity of antigen to be administered depends on the subject to be immunized and the form of the antigen. Precise amounts and form of the antigen to be administered depend on the judgment of the practitioner. However, suitable dosage ranges are readily determinable by those skilled in the art and may be of the order of micrograms to milligrams. Suitable regimes for initial administration and booster doses also are variable, but may include an initial administration followed by subsequent administrations.

In summary, the lipooligosaccharides may conventionally be used in the preparation of the medicament e.g., vaccine. In particular, the lipooligosaccharides may be formulated with a diluent or a pharmaceutically acceptable carrier e.g., a buffer or a saline. The vaccine may additionally contain usual ingredients such as a stabilizer or as already mentioned above, a mucosal adjuvant or delivery system. In a general manner, these products are selected according to standard pharmaceutical practices as described in *Remington's Pharmaceutical Sciences*, a reference book in the field.

In a vaccination protocol, the vaccine may be administered by the mucosal route, as a unique dose or preferably, several times e.g., twice, three or four times at week or month intervals, according to a prime/boost mode. The appropriate dosage depends upon various parameters, including the number of valencies contained in the vaccine, the serotypes of the lipooligosaccharides and the age of the recipient. It is indicated that a vaccine dose suitably contain per valency, from 0.5 to 100 µg, preferably from 1 to 50 µg, more preferably from 1 to 10 µg of lipooligosaccharide. A dose is advantageously under a volume of from 0.1 to 2 ml.

The vaccination protocol may be a strict mucosal protocol or a mix protocol in which the priming dose of the vaccine is administered by the mucosal e.g., intranasal route and the boosting dose(s) is (are) parenterally administered or vice versa.

Intranasal Immunization with Lipooligosaccharide-based Conjugate Vaccine from Nontypeable *Haemophilus influenzae* Inhibits Bacterial Colonization in Mouse Nasopharynx Previous studies reported as Gu, X. X. et al. 1996 *Infect Immun* 64:4047-4053 and Gu, X. X. et al. 1997 *Infect Immun* 65:4488-4493 demonstrated that systemic immunization with detoxified lipooligosaccharide (LOS) conjugate vaccines from nontypeable *Haemophilus influenzae* (NTHi) elicited LOS-specific antibodies in mice and rabbits and resulted in protection against experimental otitis media in chinchillas. In this disclosure, we investigated if intranasal immunization with such a detoxified LOS-tetanus toxoid (dLOS-TT) vaccine would generate protective immunity against NTHi in a mouse model of nasopharyngeal colonization. The results demonstrated that intranasal immunization with dLOS-TT plus adjuvant cholera toxin (CT) significantly induced LOS-specific IgA antibodies in mouse external secretions, especially in nasal wash (90-fold) followed by bronchoalveolar lavage fluid (25-fold), saliva (13-fold) and fecal extract (3-fold). LOS-specific IgA antibody forming cells were also found in mucosal and lymphoid tissues with the highest number in nasal passage (528 per $10^6$ cells). In addition, the intranasal immunization elicited a significant rise of LOS-specific IgG (32-fold) and IgA (13-fold) in serum. When these immunized mice were challenged through the nose with $10^7$ live bacteria of strain 9274, the vaccine group showed a significant reduction of NTHi by 74% and 76%, compared to that of control groups with CT alone or dLOS plus CT ($p<0.05$). Negative correlations were found between bacterial counts and the levels of nasal wash IgA or IgG, saliva IgA or serum IgG. The clearance of five heterologous strains were investigated and revealed a significant clearance in strains 3198, 5657 and 7502 but not in strains 1479 and 2019. These data indicate that intranasal immunization with dLOS-TT vaccine elicits both mucosal and systemic immunity against NTHi colonization in a mouse model of nasopharyngeal colonization. Therefore, it is envisioned as a useful strategy in humans to inhibit NTHi colonization and prevent otitis media and other respiratory diseases caused by NTHi infection.

Animals. Female BALB/c mice (6 weeks) were purchased from Taconic farms Inc. (Germantown, N.Y.). The mice were in an animal facility in accordance with National Institutes of Health guidelines under animal study protocol 1009-01.

NTHi LOS and conjugate vaccine. NTHi strain 9274 and five prototype strains 1479, 2019, 3198, 5657 and 7502 were obtained from M.A. Apicella, University of Iowa (Campagnari, A. A. et al. 1987 *Infect Immun* 55:882-887). LOS of NTHi strain 9274 was extracted from cells by hot phenol water, and then purified by gel filtration as described previously (Gu, X. X. et al. 1995 *Infect Immun* 63:4115-4120). Protein content was about 1% and nucleic acid content was less than 1%. Detoxification of the LOS, conjugation of dLOS to TT, and characterization of dLOS-TT from strain 9274 were described previously (Gu, X. X. et al. 1996 *Infect Immun* 64:4047-4053). The composition of dLOS-TT was 638 µg of dLOS and 901 µg of TT per ml with a molar ratio of dLOS to TT at 35:1.

Bacterial growth and LOS purification. NTHi 9274, isolated from middle ear fluid removed from a patient with OM, was provided by M. A. Apicella, University of Iowa. The strain was grown on chocolate agar at 37° C. under 5% $CO_2$ for 8 h and transferred to 200 ml of 3% brain heart infusion medium (Difco Laboratories, Detroit, Mich.) containing NAD (5 µg/ml) and hemin (2 µg/ml) (Sigma Chemical Co., St. Louis, Mo.) in a 500-ml bottle. The bottle was incubated at 150 rpm in an incubator shaker (model G-25; New Brunswick Scientific, Co. Edison, N.J.) at 37° C. overnight. The culture was transferred to five 2.8-liter baffled Fernbach flasks, each of which contained 1.4 liters of the same medium. The flasks were shaken at 140 rpm and maintained at 37° C. for 24 h. The culture was centrifuged at 15,000×g at 4° C. for 30 min to separate the cells and the supernatant. LOS was purified from cells by a modified phenol-water extraction (Gu, X. X. et al. 1995 *Infect Immun* 63:4115-4120) and from the culture supernatant by gel filtration (Gu, X. X. and Tsai, C. M. 1993 *Anal Biochem* 196:311-318). The protein and nucleic acid contents of both purified LOSs were less than 1% (Smith, P. K. et al. 1985 *Anal Biochem* 150:76-85; Warburg, O. and W. Christian 1942 *Biochem Z* 310:385-421).

Detoxification of LOS. Anhydrous hydrazine treatment of lipopolysaccharides (LPSs) under mild condition removes esterified fatty acids from lipid A (Gupta, R. K. et al. 1992 *Infect Immun* 60:3201-3208). LOS (160 mg), each lot, was dried over $P_2O_5$ for 3 days, suspended in 16 ml of anhydrous hydrazine (Sigma), and incubated at 37° C. for 2 h with mixing every 15 min. This suspension was cooled on ice and added dropwise to cold acetone in an ice bath until a precipitate formed ($\geqq$90% acetone). The mixture was centrifuged at 5,000×g at 5° C. for 30 min. The pellet was washed twice with cold acetone and dissolved in pyrogen-free water at a final concentration of 20 mg/ml. The reaction mixture was ultracentrifuged at 150,000×g at 5° C. for 3 h. The supernatant was freeze-dried and passed through a column (1.6 by 90 cm) of Sephadex G-50 (Pharmacia LKB Biotechnology, Uppsala, Sweden), eluted with 25 mM ammonium acetate, and monitored with a differential refractometer (R-400; Waters, Milford, Mass.). The eluate was assayed for carbohydrate by the phenol-sulfuric acid method (Dubois, M. et al. 1956 *Anal Biochem* 28:250-256). The carbohydrate-containing fractions were pooled, freeze-dried three times to remove the salt, and designated dLOS. The yields of the dLOS from three lots ranged from 48 to 55% by weight. For all material and reagent preparations, glassware was baked and pyrogen-free water was used.

Derivatization or dLOS. Adipic acid dihydrazide (ADH) (Aldrich Chemical Co., Milwaukee, Wis.) was bound to the carboxyl group of the KDO moiety of the dLOS to form adipic hydrazide (AH)-dLOS derivatives with 1-ethy-3-(3-dimethylaminopropyl)carbodiimide HCl (EDC) and N-hydroxysulfosuccinimide (Pierce) (Gu, X. X. and C. M. Tsai 1993 *Infect Immun* 61:1873-1880; Staros, J. V. et al. 1986 *Anal Biochem* 156:220-222). dLOS (70 mg) was dissolved in 7 ml of 345 mM ADH (the molar ratio of ADH to LOS is ~100:1 based on an estimated 3,000 $M_r$ for dLOS) (Gibson, B. W. et al. 1993 *J Bacteriol* 175:2702-2712; Helander, J. M. et al. 1988 *Eur J Biochem* 177:483-492). N-Hydroxysulfosuccinimide was added to a concentration of 8 mM, the pH was adjusted to 4.8 with 1 M HCl, and EDC was added to a concentration of 0.1 M. The reaction mixture was stirred and maintained at pH 4.8±0.2 with 1 M HCl for 3 h at room temperature. It was adjusted to pH 7.0 with NaOH and passed through the G-50 column as described above. The eluate was assayed for carbohydrate and for AH by a modification of a previously described method (Kemp, A. H. and M. R. A. Morgan 1986 *J Immunol Methods* 94:65-72) by measuring the $A_{490}$ of AH groups. The peaks containing both carbohydrate and AH were pooled, freeze-dried three times to remove the salt, and designated AH-dLOS. AH-dLOS was measured for its composition with dLOS and ADH as standards (Dubois, M. et al. 1956 *Anal Biochem* 28:250-256; Kemp, A. H. and M. R. A. Morgan 1986 *J Immunol Methods* 94:65-72).

Conjugation of AH-dLOS to proteins. TT was obtained from Connaught Laboratories, Inc., Swiftwater, Pa. HMP was purified from NTHi 12 (Barenkamp, S. J. 1996 *Infect Immun* 64:1246-1251). AH-dLOS was coupled to carboxyl groups on TT or HMP at pH 5.6 with EDC. AH-dLOS (20 mg) was dissolved in 2 ml of water and mixed with 10 mg of TT (5.9 mg/ml) or with 8 mg of HMP (4 mg/ml). The molar ratio of AH-dLOS to both TT ($M_r$ 150,000) and HMP ($M_r$ 120,000) was ~100:1. The pH was adjusted to 5.6 with 0.1 M HCl, and EDC was added to a concentration of 0.1 M. The reaction mixture was stirred for 1 to 3 h at room temperature; the pH was maintained at 5.6±0.2 with 0.1 M HCl. The reaction mixture was adjusted to pH 7.0, centrifuged at 1,000×g for 10 min, and passed through a column (1.6 by 90 cm) of Sephacryl S-300 in 0.9% NaCl. Peaks that contained both protein and carbohydrate were pooled and designated dLOS-TT or dLOS-HMP. Both conjugates were analyzed for their composition of carbohydrate and protein with dLOS and bovine serum albumin (BSA) as standards (Dubois, M. et al. 1956 *Anal Biochem* 28:250-256; Smith, P. K. et al. 1985 *Anal Biochem* 150:76-85).

Immunization and sample collection. Mice were immunized nasally with 10 µl of phosphate-buffered saline (PBS) containing a mixture of 5 µg of dLOS-TT and 1 µg of cholera toxin (List Biological Laboratories, Campbell, Calif.) as an adjuvant. Control mice intranasally received 10 µl of PBS containing 5 µg of dLOS and/or 1 µg of CT. Each dose was pipetted into the mouse nostril (5 µl each side) under anesthesia with intraperitoneal injection of 0.1 ml of 2% ketamine and 0.2% xylazine. Immunizations were given 5 times on days 0, 7, 14, 21 and 28. On day 35, one set of mice was used for bacterial challenge while another set was used for sample collections only described as follows. Nasal washes, saliva, bronchoalveolar lavage fluids (BALFs), fecal extracts, and sera were collected from mice of each group under anesthesia as described before (Kurono, Y. et al. 1999 *J Infect Dis* 180: 122-132). Briefly, salivary samples were obtained following intraperitoneal injection with 0.1 ml of 0.1% pilocarpine (Sigma, St. Louis, Mo.) in PBS to induce salivary secretion. Blood samples were collected from axillary artery. After removal of the mandible, the nasal cavity was gently flushed from posterior opening of the nose with 200 µl of PBS and nasal washes were collected from the anterior openings of the nose. BALF was obtained by irrigation with 1 ml of PBS through a blunted needle inserted into the trachea after incision. Fecal extract samples were obtained by adding weighed pellets to PBS containing 0.01% sodium azide (100 mg of fecal samples/ml) according to the method of deVos and Dick (Gu, X. X. et al. 1996 *Infect Immun* 64:4047-4053). Blood and fecal samples were centrifuged, and the supernatants were collected.

Preparation of single cell suspension. On day 35, nasal passages, nasal-associated lymphoid tissues (NALTs), spleens, cervical lymph nodes (CLNs), lungs, small intestines and submandibular glands (SMGs) were collected from mice. Single cell suspensions were prepared from nasal passages, NALTs, spleens, CLNs, lungs and SMGs by a gentle teasing through stainless steel mesh (Asanuma, H. et al. 1997 *J Immunol Methods* 202:123-131). Small intestines were dissociated with 0.5 mg/ml collagenase Type IV (Sigma) to obtain single-cell suspensions after removal of Peyer's patches. Each single-cell suspension sample except for NALTs, spleens and CLNs was centrifuged over a discontinuous Percoll gradient (Pharmacia, Uppsala, Sweden), and mononuclear cells (MNCs) at the interface of the 40% and 75% layers were collected. Then, MNCs were suspended in complete medium (1 liter of RPMI1640 supplemented with 1% of nonessential amino acid solution, 1 mM HEPES, 100,000 U of penicillin, 100 µg of streptomycin, 40 mg of gentamicin, and 10% fetal calf serum). The number and viability of MNCs were examined by trypan blue dye exclusion.

Detection of LOS-specific antibodies by ELISA. Specific anti-LOS antibodies in nasal wash, saliva and serum were determined by ELISA with strain 9274 LOS as coating antigen (10 µg/ml) (Gu, X. X. et al. 1996 *Infect Immun* 64:4047-4053). Samples of naive mice were served as negative controls. The negative controls gave optical density readings of less than 0.1 for IgA, IgG and IgM in serum, and 0.01 in external secretions. The antibody endpoint titer was defined as the highest dilution of samples giving an optical density two-fold greater than that of the negative controls at 30 min.

Detection of LOS-specific antibody-forming cells (AFCs) by enzyme-linked immunospot (ELISPOT) assay. For the enumeration of LOS-specific immunoglobulin-producing cells, the numbers of LOS-specific IgA-, IgG-, and IgM-producing cells in NALT, NP, SMG, spleen, CLN, lung, and small intestine were determined with ELISPOT assay (Kodama, S. et al. 2000 *Infect Immun* 68:2294-2300.). Briefly, 96-well filtration plates with a nitrocellulose base (Millititer HA; Millipore Corp., Bedford, Mass.) were coated with 100 µl of strain 9274 LOS (10 µg/ml) and incubated overnight at 4° C. The plates were washed three times with PBS and then blocked with complete medium for 1 h. After removing the blocking medium, test cells in complete medium were added at various concentrations and cultured at 37° C. with 5% $CO_2$ for 6 h. After the incubation, the plates were washed thoroughly with PBS and then with PBS containing 0.05% Tween 20 (PBS-T). For capture of secreting antibodies, biotinylated goat anti-mouse IgA, IgG, or IgM (Sigma) was added in PBS-T at 1:1,000. After overnight incubation at 4° C., the plates were washed five times with PBS-T, and incubated with 5 µg/ml of avidin-peroxidase conjugates (Sigma) in PBS-T for 1 h at room temperature. After washing with PBS-T and PBS three times for each, spots were developed in 4-chloro-1-naphthol solution for 10 min. The reaction was stopped by washing with water. The plates were dried and dark blue-purple colored spots were counted as LOS-specific AFCs under a stereo microscope.

Immunohistochemistry for IgA-, IgG-, IgM-positive cells in the nose. For histological observation, the mice were euthanized on day 35 and then perfused transcardially with PBS, followed by perfusion with 10% neutral buffered formalin. Mouse heads were removed and fixed in 10% formalin for 6 hr and decalcified with 0.12 M ethylenediamine tetraacetic acid (EDTA, pH 7.0) for 2 weeks. After dehydration, the tissues were embedded in paraffin. For detection of IgA, IgG, IgM-positive cells in the nose, vertical-serial section (6 µm thickness) were prepared. Specimens were dehydrated through a graded series of ethanol and treated with 3% hydrogen peroxide in absolute methanol for 30 min. Sections were exposed to 5% normal goat serum in PBS for 30 min and then incubated overnight with biotinylated goat anti-mouse IgA, IgG, or IgM in 1% bovine serum albumin (BSA)-PBS. After rinsing with PBS, sections were incubated with avidin-biotin complex (Vector Laboratories, Burlingame, Calif.) for 1 h and developed in 0.05% 3,3'-diaminobenzidine-0.01% $H_2O_2$ substrate medium in 0.1M PBS for 8 min.

Bacterial challenge in nasopharynx. To examine the effect of the dLOS-TT vaccine on NTHi clearance in nasopharynx, the mice immunized with different antigens were challenged with the homologous strain 9274. The strain was grown on chocolate agar at 37° C. under 5% $CO_2$ for 16 h, and then 3-5 clones were transferred to another plate and incubated for 4 h. A bacterial suspension was prepared to the concentration of $4\sim6\times10^6$ CFU/ml in PBS and stored on ice until use. The bacterial concentration was determined by a 65% transmission at wavelength 540 nm, and confirmed by counting the colonies after overnight incubation. The mice were intranasally inoculated with 10 µl of the bacterial suspension on day 35. Six hours postchallenge, nasal washes were collected and diluted serially in PBS, and 50 µl of the diluted samples were plated on chocolate agar. Bacterial colonies were counted after overnight incubation. To investigate correlation between antibody levels and bacterial clearance of strain 9274, saliva, BALF, fecal extract and serum samples were collected from each mouse simultaneously. To examine the effect of the vaccine on heterologous NTHi, strains 1479, 2019, 3198, 5657 and 7502 were used based on the same procedure except only one control group (CT) was included since no significant difference was found between control groups.

Whole cell ELISA. To examine the cross-reactivity of antibodies in nasal wash (IgA) and sera (IgG) elicited by the vaccine against heterologous NTHi strains, the homologous strain 9274 and strains 1479, 2019, 3198, 5657 and 7502 were suspended in PBS to an optical density of 65% transmission at 540 μm. Microtiter plates were coated with 100 μl of the suspension and evaporated at 37° C. Other steps were the same as described for the LOS ELISA except 3% of BSA-PBS was used for blocking and 1:15 dilution used for nasal wash or serum samples.

Western blot analysis. For characterization of antibodies in external secretions and sera, Western blot analysis was performed with the homologous strain 9274 and five heterologous strains. Each bacterial suspension was adjusted to a protein concentration of 2 mg/ml. The suspensions were boiled at 100° C. for 10 min in digestion buffer, subjected to SDS-PAGE in a 15% polyacrylamide gel and then transferred onto nitrocellulose membranes at 250 mA for 6 h (Gu, X. X. et al. 1992 *J Clin Microbiol* 30:2047-2053). After blocking with 3% BSA-Tris buffered saline (TBS) for 1 h, the membranes were incubated with nasal wash or serum sample (1:10) for 3 h, followed by biotinylated goat anti-mouse IgA or IgG for 2 h. The membranes were washed with TBS-T, and incubated with avidin-peroxidase conjugate for 1 h. After washing with TBS, the membranes were developed with 4-chloro-1-naphthol solution. A duplicate gel was silver-stained after SDS-PAGE.

Statistical analysis. Antibody levels were expressed as the geometric mean (GM) ELISA titers (reciprocal) of n independent observations (±SD range). AFCs were expressed as a mean of n independent observations (±SD). Bacterial concentration was expressed as GM CFU of n independent observations (±SD). Differences between vaccine and control groups were determined using Student's t-test and P values smaller than 0.05 were considered significant. Correlation between bacterial concentration and IgA or IgG titer was analyzed by Pearson's product moment method (null hypothesis: $H_0$: P=0; alternative hypothesis: $H_1$: P<0, significantly).

Results

TABLE 1

Murine antibody responses to NTHi 9274 LOS elicited by dLOS-TT conjugate

| Immunogen[a] | Isotype | GM antibody ELISA titers (±SD range)[b] | | | | |
|---|---|---|---|---|---|---|
| | | Saliva | Nasal wash | BALF[c] | Fecal Extract | Serum |
| DLOS-TT + CT | IgA | 63 (28-140)** | 452 (205-990)** | 128 (24-692)** | 16 (6-42)** | 125 (61-257)** |
| | IgG | 13 (4-38)** | 16 (8-31)** | 25 (8-27)** | 6 (4-8) | 320 (131-780)** |
| | IgM | 5 (5) | 5 (4-7) | 6 (4-11) | 5 (4-7) | 10 (10) |
| DLOS + CT | IgA | 6 (4-9) | 7 (4-12) | 6 (4-9) | 5 (5) | 12 (8-20) |
| | IgG | 5 (5) | 6 (4-8) | 6 (4-9) | 5 (5) | 10 (10) |
| | IgM | 5 (5) | 5 (5) | 5 (5) | 5 (5) | 10 (10) |
| CT | IgA | 5 (5) | 5 (5) | 5 (5) | 5 (5) | 10 (10) |
| | IgG | 5 (5) | 5 (5) | 5 (5) | 5 (5) | 10 (10) |
| | IgM | 5 (5) | 5 (5) | 5 (5) | 5 (5) | 10 (10) |

[a]Ten mice from each group were given an intranasal immunization on days 0, 7, 14, 21 and 28 with dLOS-TT + CT, dLOS + CT or CT alone. External and serum samples were collected at 1 week after the last immunization.
[b]LOS antibodies were measured by ELISA using strain 9274 LOS as a coating antigen. Symbols: dLOS-TT + CT group versus either dLOS + CT or CT group: p < 0.01.
[c]BALF: Bronchoalveolar lavage fluid.

TABLE 2

LOS-specific AFCs in mucosal and lymphoid tissues elicited by dLOS-TT conjugate

| Immunogen[a] | Isotype | LOS-specific AFCs/$10^6$ MNCs (mean ± SD)[b] | | | | | | |
|---|---|---|---|---|---|---|---|---|
| | | NALT[c] | Nasal Passage | SMG[c] | Lung | Intestine | CLN[c] | Spleen |
| dLOS-TT + CT | IgA | 27 ± 8 | 528 ± 40 | 9 ± 1 | 12 ± 2 | 6 ± 1 | 9 ± 1 | 4 ± 1 |
| | IgG | 0 | 9 ± 6 | 0 | 0 | 0 | 10 ± 8 | 3 ± 2 |
| | IgM | 0 | 0 | 0 | 0 | 0 | 0 | 0 |
| DLOS + CT | IgA | 0 | 2 ± 2 | 0 | 0 | 0 | 0 | 0 |
| | IgG | 0 | 0 | 0 | 0 | 0 | 0 | 0 |
| | IgM | 0 | 0 | 0 | 0 | 0 | 0 | 0 |
| CT | IgA | 0 | 0 | 0 | 0 | 0 | 0 | 0 |
| | IgG | 0 | 0 | 0 | 0 | 0 | 0 | 0 |
| | IgM | 0 | 0 | 0 | 0 | 0 | 0 | 0 |

[a]See Table 1, footnote a.
[b]LOS-specific AFCs were detected by ELISPOT assay using strain 9274 LOS as a coating antigen. The numbers of AFCs were obtained from each of six mice per group.
[c]NALT: nasal associated lymphoid tissue; SMG: submandibular gland; and CLN: cervical lymph node.

TABLE 3

Effect of intranasal immunization with dLOS-TT conjugate on bacterial clearance of heterologous NTHi strains from mouse nasopharynx

| Strain concentration[a] (cfu/ml) | Immunogen[b] | Bacterial recovery GM (±SD range) (cfu/ml) | Bacterial reduction (%)[c] |
|---|---|---|---|
| 1479 ($5 \times 10^9$) | dLOS-TT + CT<br>CT | 1324 (36-5676)<br>2643 (841-8303) | 50% |
| 2019 ($6 \times 10^9$) | dLOS-TT + CT<br>CT | 2870 (935-8807)<br>4054 (1369-12006) | 29% |
| 3198 ($4 \times 10^9$) | dLOS-TT + CT<br>CT | 3347 (1259-8902)<br>9727 (3336-28365) | 65%* |
| 5657 ($5 \times 10^9$) | DLOS-TT + CT<br>CT | 780 (340-1792)<br>2041 (531-7998) | 63%* |
| 7502 ($6 \times 10^9$) | DLOS-TT + CT<br>CT | 2050 (726-5793)<br>4788 (1779-12835) | 57%* |

[a]Five LOS prototype strains were used for nasopharyngeal challenge and mouse nasal washes were collected at 6 h postchallenge from 10 mice of each group.
[b]See Table 1, footnote a.
[c]dLOS-TT + CT group versus CT group, symbols: $p < 0.05$.

LOS-specific immune responses in external secretions and serum samples. LOS-specific immune responses were elicited significantly by intranasal immunization with dLOS-TT and CT but not controls (Table 1). LOS-specific IgA titers in external secretions and in serum were increased by dLOS-TT and CT, especially in nasal wash (90-fold), BALF (26-fold), saliva (13-fold) and serum (13-fold), whereas slight increase of LOS-specific IgA in fecal extract was found (3-fold) when compared to that of CT controls. LOS-specific IgG titers in serum were increased significantly with dLOS-TT and CT by 32-fold, while LOS-specific IgG antibodies in external secretions except for fecal extract were also elevated by 3 to 5-fold when compared to that of CT controls. No LOS-specific IgM was detected and no difference of antibody titers found between two control groups: dLOS plus CT and CT alone ($p > 0.05$).

LOS-specific antibody-forming cells (AFCs) in mucosal effector tissues. Intranasal immunization with dLOS-TT and CT resulted in detection of LOS-specific IgA AFCs in all tissues tested, including distant organs such as intestine and spleen (Table 2). The majority of LOS-specific IgA AFCs were located in nasal passage (528 per $10^6$ cells), followed by a small amount in other tested tissues. The dominant isotype of LOS-specific AFCs was IgA, followed by small numbers of IgG but not IgM. LOS-specific IgG AFCs were only detected in nasal passage, CLN and spleen. Intranasal immunization with dLOS and CT elicited 2 LOS-specific IgA AFCs in nasal passage but not in other tested tissues. No AFC was found in any tissues from mice immunized with CT.

Figure 3:
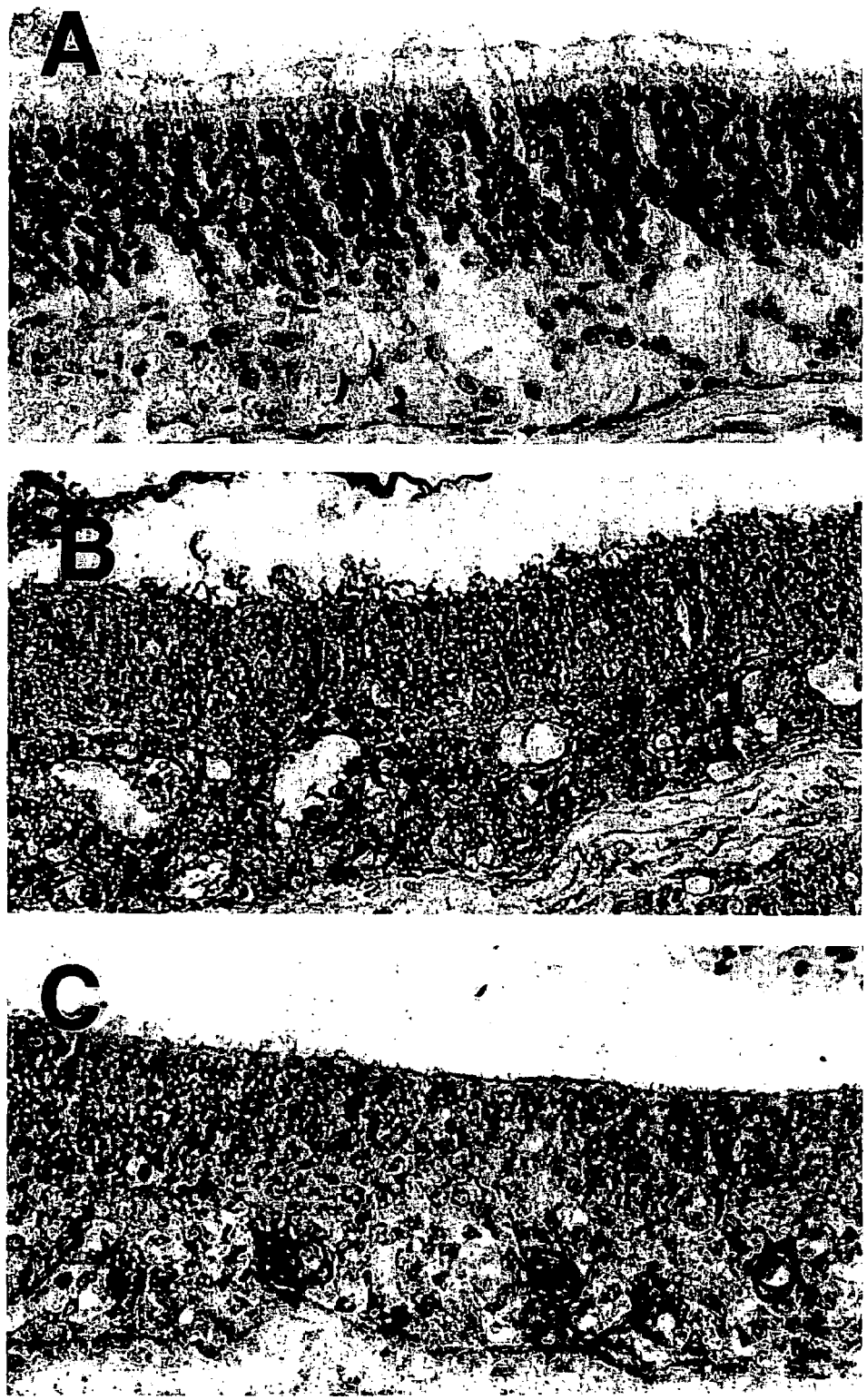
FIG. 3. Immunohistochemistry with anti-IgA and anti-IgG staining in the nose. (A) Anti-IgA (or anti-IgG) staining in control mice, (B) anti-IgA staining in dLOS-TT immunized mice, and (C) anti-IgG staining in dLOS-TT immunized mice (magnification 400x). Intranasal immunization with dLOS-TT dramatically increased the staining with IgA of the mucous blanket, and glandular cells in the nose as compared with the staining in the control mice. However, staining with anti-IgG was strongly shown only at the vessels of the nasal tissue in mice immunized with dLOS-TT. The nasal tissue of the control mice was not stained with anti-IgA (or anti-IgG).

Immunohistochemical staining of the nose. Immunohistochemical staining of noses with anti-IgA (FIG. 3) revealed that the mouse immunized with the dLOS-TT vaccine showed positive staining in the mucous blanket and glandular tissues (B) as compared with the control mouse (A). A large number of IgA-positive cells were found in nasal subepithelial layer and nasal glands. In contrast, staining with anti-IgG in the mouse immunized with the dLOS-TT vaccine was only seen in the area of the vessels but not the glandular tissue (C). The nasal mucosa of the control mice was not stained with anti-IgG, and both vaccine-immunized and control mice showed no staining with anti-IgM in the nose.

Figure 4:
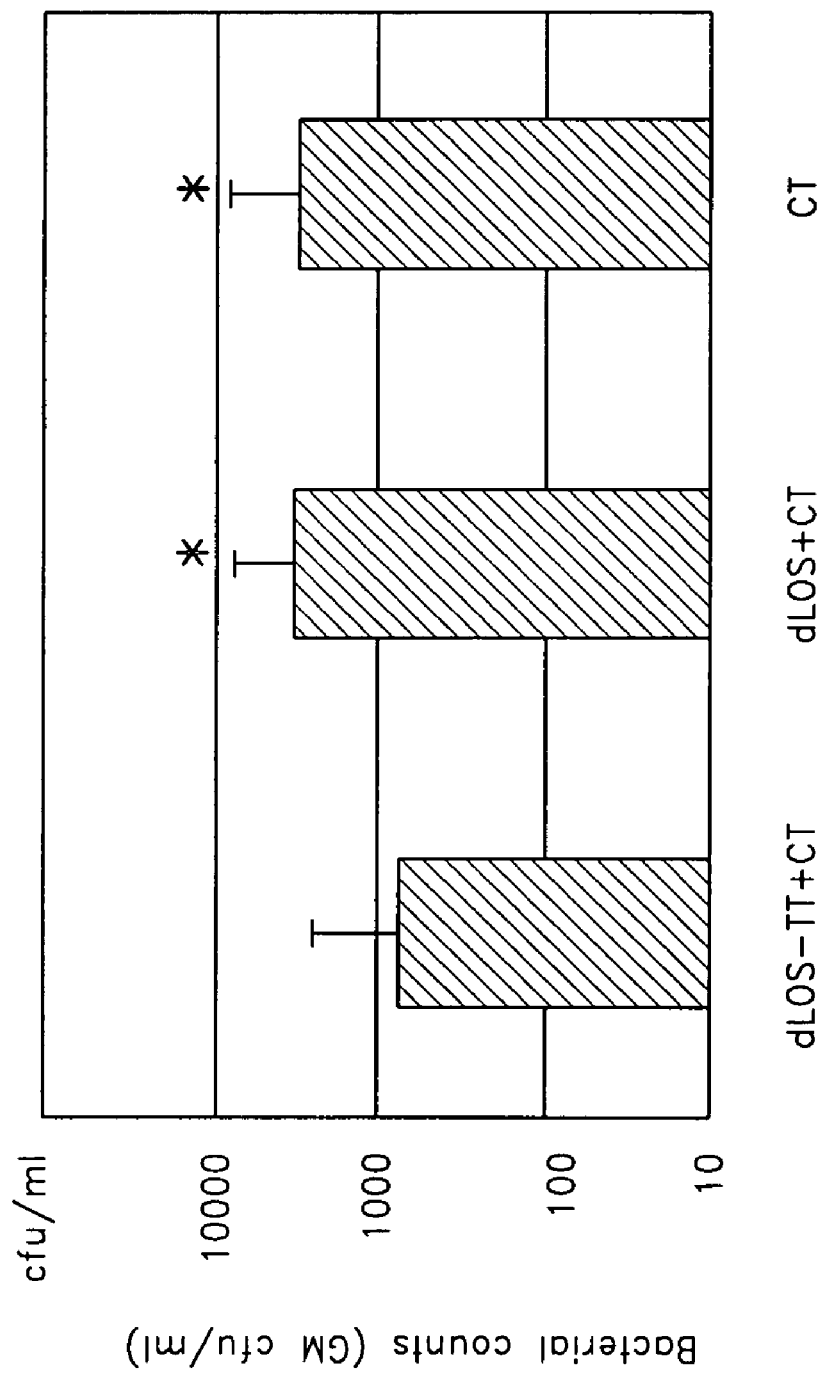
FIG. 4. Bacterial clearance of NTHi strain 9274 from mouse nasopharynx. Immunization schedules and mouse grouping were shown in Table 1, footnote a. Mice were challenged with strain 9274 into the nose 1 wk after the last immunization and nasal washes were collected at 6 h post-challenge. Mice immunized with dLOS-TT and CT showed a significant reduction of bacterial recovery by 74% or 76% when compared to those of the mice immunized with CT alone or dLOS and CT (*, p<0.05).

Bacterial clearance from nasopharynx. Since intranasal immunization with dLOS-TT vaccine induced high levels of LOS-specific IgA antibodies in nasal wash and IgG antibodies in serum, it was important to examine whether the NTHi LOS specific immune responses contributed to the clearance of NTHi colonization in the nasal tract. Bacterial colonization of the homologous strain inoculated into the mouse nasopharynx is shown in FIG. 4. The mice immunized with dLOS-TT and CT showed a significant reduction of bacterial recovery by 74% or 76% when compared to those of the mice immunized with CT alone or dLOS and CT ($p < 0.05$). Relationship between LOS-specific antibody titers and bacterial counts from nasopharynx was further analyzed in nasal wash, saliva, BALF, fecal extract and serum from dLOS-TT and CT immunized and CT immunized mice. Negative correlation with bacteria was found in nasal wash IgA ($r = -0.56$, $p = 0.0085$) or IgG ($r = -0.63$, $p = 0.0025$), saliva IgA ($r = -0.45$, $p = 0.0447$), or serum IgG ($r = -0.65$, $p = 0.014$).

Heterologous bacterial clearance from nasopharynx. Since strain 9274 LOS contains common LOS epitopes, bacterial clearance of heterologous strains was performed in mice immunized with or without dLOS-TT in CT (Table 3). Significant inhibition in bacterial colonization was seen in 3 out of 5 strains (3198, 5657 and 7502) with a reduction of 57 to 65%, when compared to the mice immunized with CT alone ($p < 0.05$).

Figure 5:
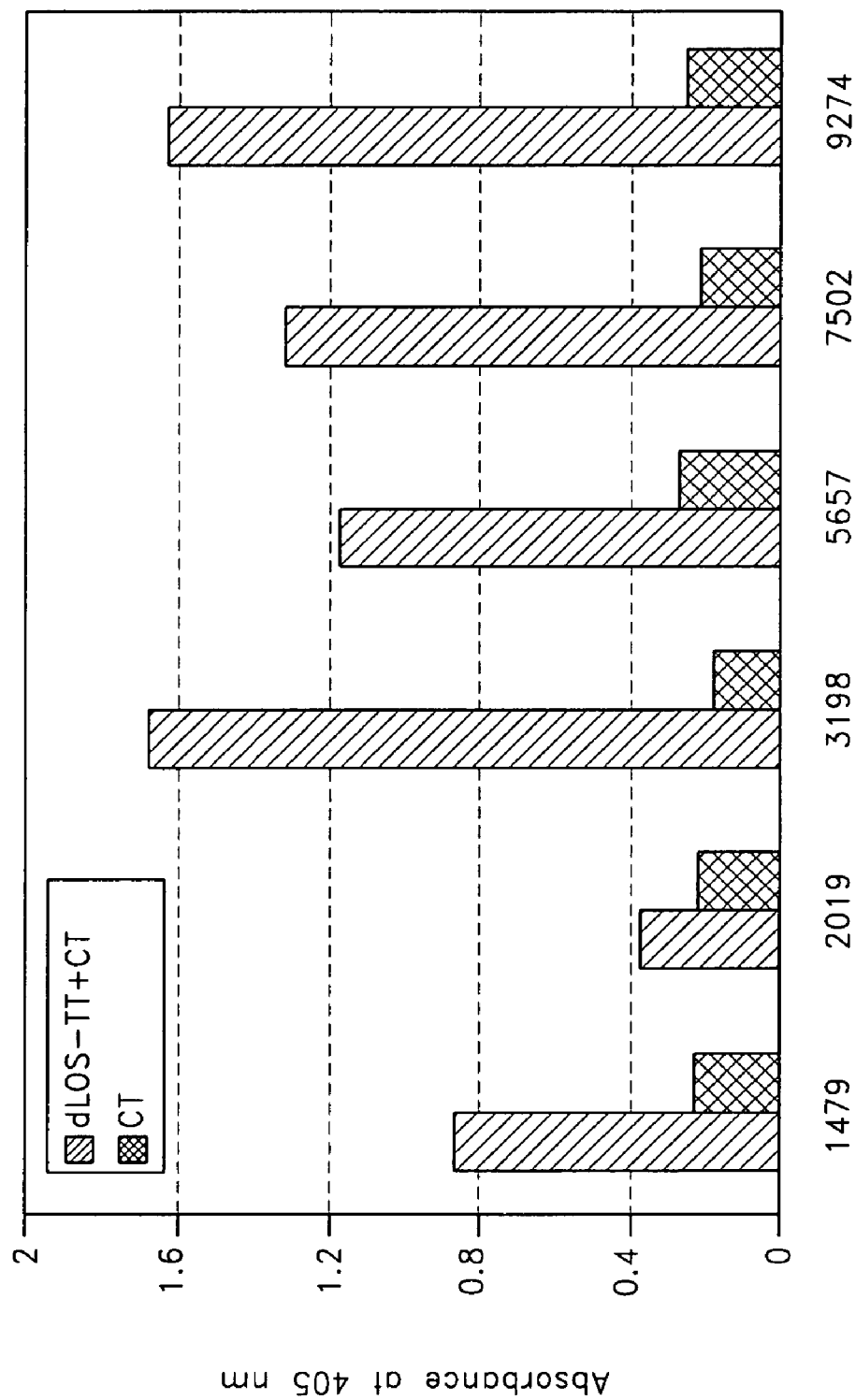
FIG. 5. Binding reactivity of nasal wash (IgA) to homologous strain and five heterologous strains in whole-cell ELISA. The nasal wash from mice immunized with dLOS-TT bound strongly to the homologous strain 9274 and the heterologous strains 3198, 5657 and 7502 but weakly to strains 1479 and 2019.
Figure 6:
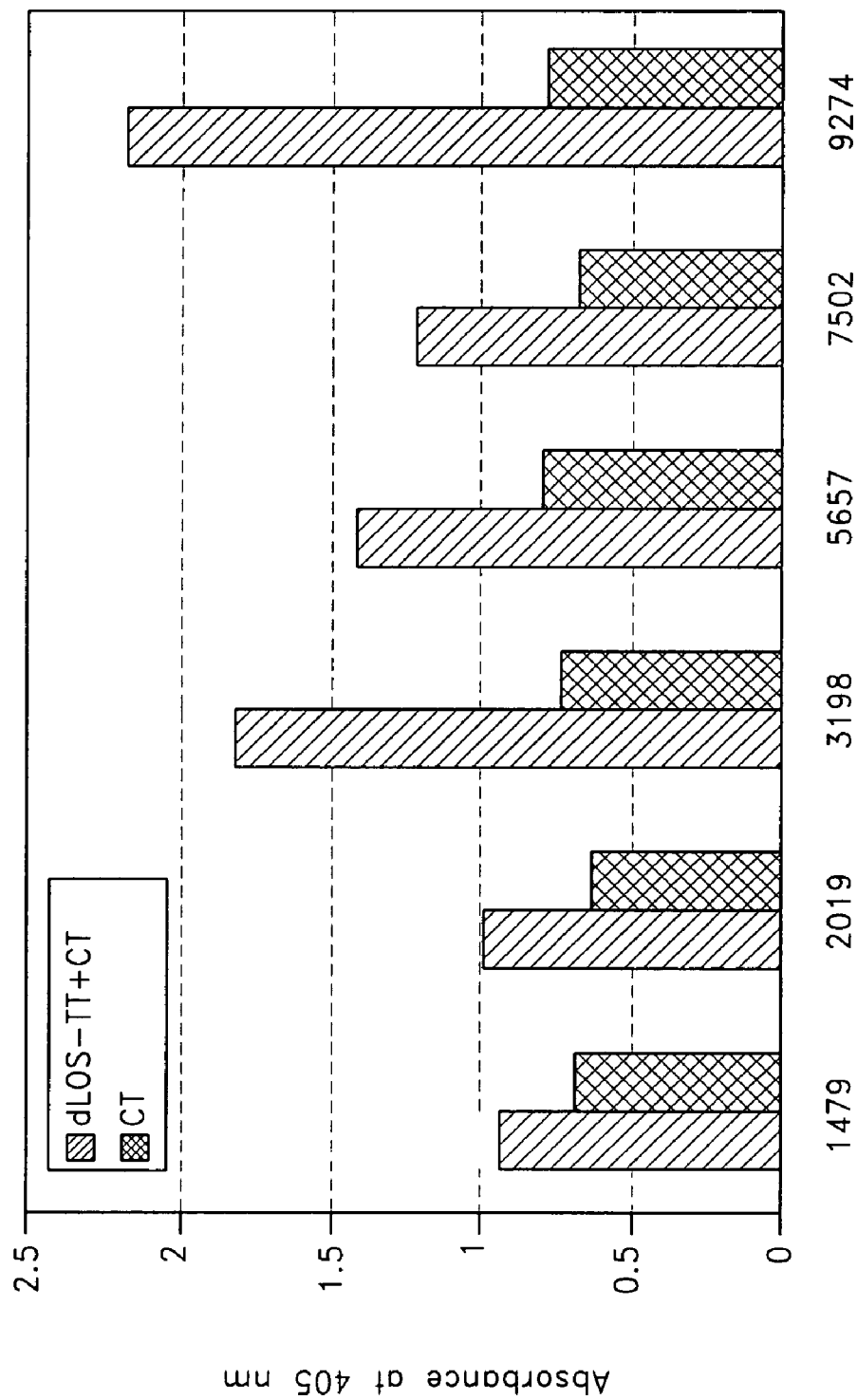
FIG. 6. Binding reactivity of serum (IgG) to homologous strain and five heterologous strains in whole-cell ELISA. The observed binding reactivity was similar to the one observed in nasal wash from mice immunized with the dLOS-TT (FIG. 5).
Figure 7:
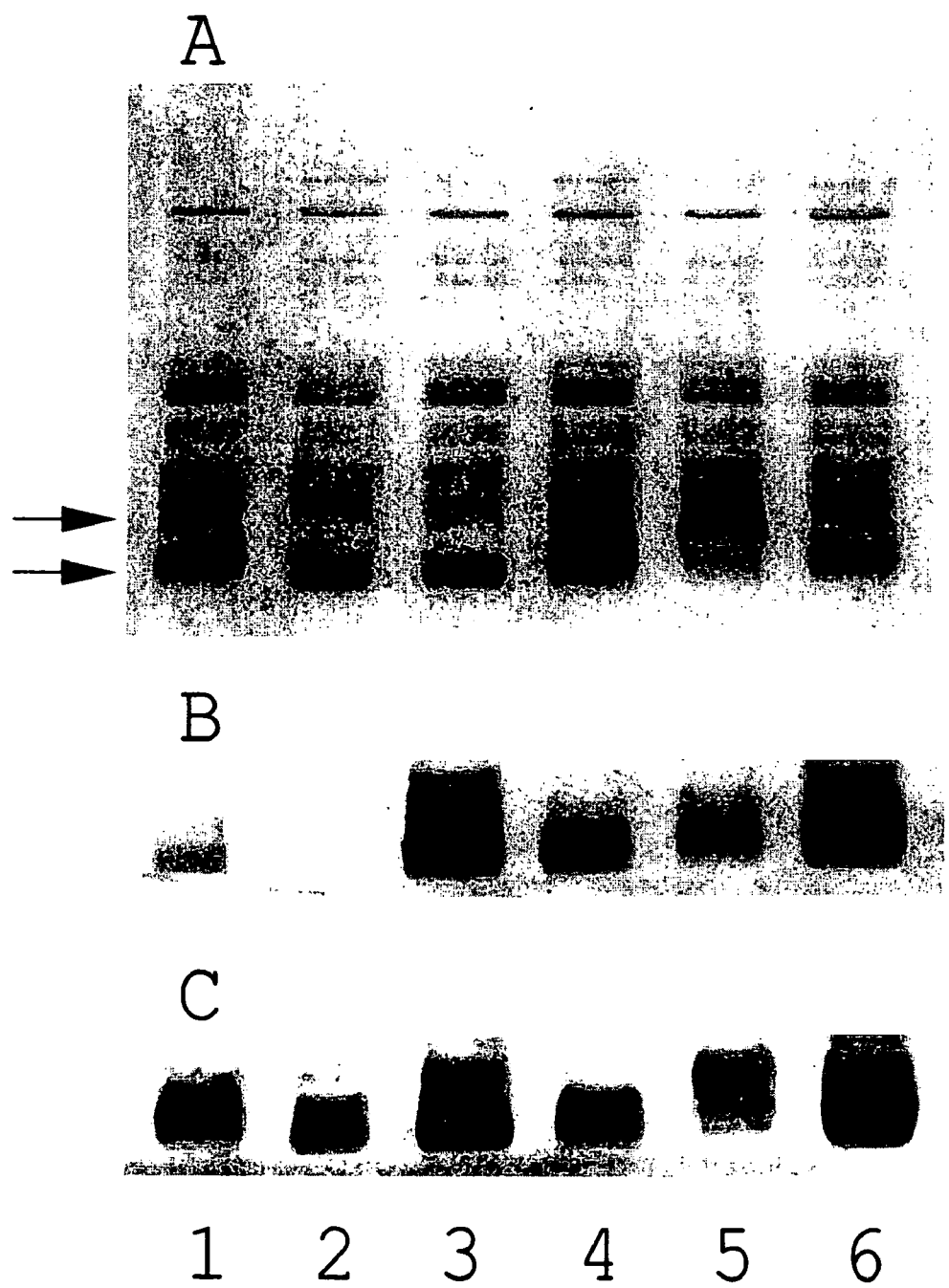
FIG. 7. Silver-stained SDS-PAGE patterns (A) and Western blot analysis (B and C) of homologous strain and five heterologous strains. Lanes 1 through 6 contain strains 1479, 2019, 3198, 5657, 7502 and 9274. Nasal wash (IgA) from mice immunized with dLOS-TT was reactive strongly to LOSs from strains 9274, 3198, 5657, and 7502, weakly to 1479 but not to 2019 (B). However, sera (IgG) from mice immunized with the dLOS-TT were reactive to all LOSs with strong binding in strains 9274, 3198, 5657 and 7502 (C). Arrows show each LPS of Ra (upper arrow) and Rc (lower arrow) mutants as markers from *Salmonella minnesota*.

Cross-reactivity of LOS antibodies with heterologous strains. The cross-reactivity of antibodies elicited by NTHi 9274 dLOS-TT and CT against heterologous strains was analyzed by whole cell ELISA with both nasal wash (mainly IgA) and sera (mainly IgG) (FIGS. 5 and 6). Nasal wash IgA bound strongly to not only the homologous strain but also the heterologous strains 3198, 5657, and 7502 when compared with the controls. Binding reactivity of serum IgG also showed the same tendency as the nasal wash IgA. However, bindings to the heterologous strains 1479 and 2019 were weak in both nasal wash and serum antibodies. The control mice showed low background binding in nasal wash and medium background in serum to all strains. Both nasal wash and serum samples were further tested in Western blot with all above strains (FIG. 7). Nasal wash IgA from mice immunized with dLOS-TT and CT was reactive strongly to LOSs of strains 9274 and 3198, moderately to 5657 and 7502, and weakly to 1479 LOS but not 2019 LOS. However, the serum IgG was reactive to all with a strong binding to LOSs of strains 9274 and 3198.

Conclusions. Intranasal immunization with a NTHi dLOS-TT conjugate vaccine elicited LOS-specific IgA antibodies in local and distant external secretions as well as LOS-specific IgA AFCs in mucosal effector tissues (nasal passage, SMG, lung and intestine) and lymphoid tissues (NALT, CLN and spleen). It also generated significant LOS-specific IgG antibodies in serum. This is the first demonstration at intranasal administration of a LOS-based conjugate eliciting antigen-specific mucosal and systemic immune responses although several recent studies have shown similar results by capsular polysaccharide conjugates from Streptococcal pneumoniae, group B Streptococci or Haemophilus influenzae type b (Bergquist, C., T. Lagergard, and J. Holmgren 1998 Apmis 106:800-806; Jakobsen, H. et al. 1999 Infect Immun 67:4128-4133; Jakobsen, H. et al. 1999 Infect Immun 67:5892-5897; Shen, X. et al. 2000 Infect Immun 68:5749-5755). In summary, intranasal immunization with a LOS-based conjugate vaccine elicited LOS-specific mucosal and systemic immunity, which inhibited not only the homologous but also the heterologous bacterial adherence in a mouse model of nasopharyngeal colonization. Therefore, it is envisioned as being effective in humans with an appropriate mucosal adju- Intranasal Immunization with Detoxified
Lipooligosaccharides from *Moraxella catarrhalis*
Conjugated to a Protein Elicits Protection in a Mouse
Model of Colonization

*Moraxella catarrhalis* is a significant cause of otitis media in children. Lipooligosaccharide (LOS) is a major surface antigen of *M. catarrhalis* and a potential vaccine candidate. In order to address the mucosal immunity of detoxified LOS (dLOS)-protein conjugate vaccines and their potential roles on mucosal surfaces, BALB/c mice were immunized intranasally with a mixture of dLOS-CRM (the diphtheria toxin cross-reactive mutant protein) and cholera toxin (CT) as an adjuvant, dLOS plus CT, or CT only. After immunization, the animals were aerosolly challenged with *M. catarrhalis* strain 25238. Immunization with dLOS-CRM generated a significant increase in secreting IgA and IgG in nasal washes, lung lavage and saliva, and serum IgG, IgM and IgA against LOS of *M. catarrhalis* as detected by an indirect enzyme-linked immunosorbent assay (ELISA). The dLOS-CRM also elicited LOS-specific IgA, IgG, and IgM antibody-forming cells (AFCs) in different lymphoid tissues as measured by an enzyme-linked immunospot (ELISPOT) assay. LOS-specific IgA AFCs were found in the nasal passages, spleens, nasal-associated lymphoid tissues (NALT), cervical lymph nodes (CLN), lungs, and small intestines. LOS-specific IgG and IgM AFCs were only detected in the spleens, CLN and nasal passages. Furthermore, the dLOS-CRM vaccine generated a significant bacterial clearance in the nasopharynx and lungs when compared to the controls (P<0.01) following an aerosol challenge with the homologous strain 25238. A comparison of dLOS-CRM, dLOS-TT and dLOS-UspA through intranasal immunization resulted in similar protection against *M. catarrhalis*. Intriguingly, intranasal immunization with dLOS-CRM containing CT showed a higher level of bacterial clearance in both sites when compared to subcutaneous injections with dLOS-CRM plus CT adjuvant. These data indicate that dLOS-CRM induces specific mucosal and systemic immunity against *M. catarrhalis* through intranasal immunization, and provides effective bacterial clearance in the mouse nasopharynx and lungs. Therefore, it is envisioned as being an efficient route for vaccines to prevent otitis media and lower respiratory tract infections caused by *M. catarrhalis*.

Animals. Female BALB/c mice (6-8 weeks old) were purchased from Taconic farms Inc. (Germantown, N.Y.).

Conjugate vaccine. Purification of LOS from *M. catarrhalis* strain 25238, detoxification of the LOS, and conjugation of dLOS to carrier protein including CRM, TT, UspA were performed as described previously (Gu, X. X. et al. 1998 *Infect Immun* 66:1891-1897).

LOS purification. Type A strain ATCC 25238 was grown on chocolate agar at 37° C. in 5% $CO_2$ for 8 h and transferred to 250 ml of 3% tryptic soy broth (Difco Laboratories, Detroit, Mich.) in a 500-ml bottle. The bottle was incubated at 110 rpm in an incubator shaker (model G-25; New Brunswick Scientific Co., Edison, N.J.) at 37° C. overnight. The culture was transferred to six 2.8-liter baffled Fernbach flasks, each of which contained 1.4 liters of tryptic soy broth. The flasks were shaken at 110 rpm and maintained at 37° C. for 24 h. The culture was centrifuged at 15,000×g and 4° C. for 10 min to collect the cells. The cell pellets were washed once with 95% ethanol, twice with acetone, and twice with petroleum ether (Masoud, H. et al. 1994 *Can J Chem* 72:1466-1477) and dried to a powder. The LOS was extracted from cells (Gu, X. X. et al. 1995 *Infect Immun* 63:4115-4120), and the protein and nucleic acid contents of the LOS were less than 1% (Smith, P. K. et al. 1985 *Anal Biochem* 150:76-85; Warburg, O., and W. Christian. 1942 Biochem Z 310:384-421).

Detoxification of LOS. Anhydrous hydrazine treatment of LOS removes esterified fatty acids from lipid A (Gu, X. X. et al. 1996 *Infect Immun* 64:4047-4053; Gupta, R. K. et al. 1992 *Infect Immun* 60:3201-3208). LOS (160 mg) was suspended in 16 ml of anhydrous hydrazine (Sigma Chemical Co., St. Louis, Mo.) and incubated at 37° C. for 3 h with mixing. This suspension was cooled on ice and added dropwise with cold acetone until a precipitate formed. The mixture was centrifuged at 5,000×g and 5° C. for 30 min. The pellet was washed twice with cold acetone, dissolved in pyrogen-free water at a final concentration of 10 to 20 mg/ml, and then ultracentrifuged at 150,000×g and 5° C. for 3 h. The supernatant was passed through a column (1.6 by 90 cm) of Sephadex G-50 (Pharmacia LKB Biotechnology, Uppsala, Sweden) eluted with 25 mM ammonium acetate and monitored with a differential refractometer (R-400; Waters, Milford, Mass.). The eluate was assayed for carbohydrate by a phenol-sulfuric acid method (Dubois, M. et al. 1956 *Anal Biochem* 28:250-256). The carbohydrate-containing fractions were pooled, freeze-dried, and designated dLOS.

Derivatization of dLOS. Adipic acid dihydrazide (ADH; Aldrich Chemical Co., Milwaukee, Wis.) was bound to dLOS to form adipic hydrazide (AH)-dLOS derivatives, using 1-ethyl-3-(3-dimethylaminopropyl) carbodiimide HCl (EDC) and N-hydroxysulfosuccinimide (sulfo-NHS) (Pierce) (Gu, X. X., and C. M. Tsai 1993 *Infect Immun* 61:1873-1880). dLOS (70 mg) was dissolved in 7 ml of 345 mM ADH (molar ratio of ADH to LOS is ~100 to 1, based on an estimated $M_r$ of 3,000 for dLOS) (Edebrink, P. 1994 *Carbohydr Res* 257:269-284). Sulfo-NHS was added to a concentration of 8 mM, the pH was adjusted to 4.8, and EDC was added to a concentration of 0.1 M. The reaction mixture was stirred and maintained at pH 4.8 for 3 h. The reaction mixture was adjusted to pH 7.0 and passed through the G-50 column as described above. The eluate was assayed for carbohydrate and for AH (Kemp, A. H., and M. R. A. Morgan 1986 *J Immunol Methods* 94:65-72). The peaks containing both carbohydrate and AH were pooled, freeze-dried, and designated AH-dLOS. AH-dLOS was measured for its composition, using dLOS and ADH as standards (Dubois, M. et al. 1956 *Anal Biochem* 28:250-256; Kemp, A. H., and M. R. A. Morgan 1986 *J Immunol Methods* 94:65-72).

Conjugation of AH-dLOS to proteins. TT was obtained from Connaught Laboratories Inc., Swiftwater, Pa., and HMP was purified from NTHi strain 12 (Barenkamp, S. J. 1996 *Infect Immun* 64:1246-1251). AH-dLOS was coupled to TT or HMP to form conjugates (Gu, X. X., and C. M. Tsai 1993 *Infect Immun* 61:1873-1880). Briefly, AH-dLOS (30 mg) was dissolved with 3 ml of water and mixed with 15 mg of TT (5.9 mg/ml) or with 12 mg of HMP (4 mg/ml). The molar ratio of AH-dLOS to both TT ($M_r$, 150,000) and HMP ($M_r$, 120,000) was ~100 to 1. The pH was adjusted to 5.4, and EDC was added to a concentration of 0.05 to 0.1 M. The reaction mixture was stirred, and the pH was maintained at 5.4 for 3 h. The reaction mixture was adjusted to pH 7.0, centrifuged, and passed through a column (1.6 by 90 cm) of Sephacryl S-300 in 0.9% NaCl. Peaks that contained both protein and carbohydrate were pooled and designated dLOS-TT or dLOS-HMP. Both conjugates were analyzed for their composition of carbohydrate and protein, using dLOS and bovine serum albumin (BSA) as standards (Dubois, M. et al. 1956 *Anal Biochem* 28:250-256; Smith, P. K. et al. 1985 *Anal Biochem* 150:76-85).

Immunization and sample collection. Mice, 6-8 for each group, were immunized intranasally (i.n.) 4 times, or subcutaneously (s.c.) 3 times, with PBS or 5 µg of dLOS-protein at 1~2-week intervals, respectively. The total volume of administration is 10 µl for i.n. inoculation, or 0.2 ml for s.c. injection with or without Ribi 700 (25 µg/mouse) or cholera toxin (CT, 1 µg/mouse) adjuvant. One week after the last immunization, nasal washes, saliva, lung lavage, fecal extracts, and sera were collected.

Detection of LOS-specific antibodies by ELISA. The titers of LOS specific antibodies in nasal washes, saliva, lung lavage, fecal extracts and sera were determined by ELISA using *M. catarrhalis* strain 25238 LOS as a coating antigen. The antibody endpoint titer was defined as the highest dilution of sample giving an A405 twofold greater than that of negative controls.

Detection of LOS-specific antibody-forming cells (AFCs). Mononuclear cells were taken from the nasal passage, spleen, nasal-associated lymphoid tissue, cervical lymph node, Peyer's patch and lung. Numbers of LOS-specific IgA-, IgG-, and IgM-producing cells in each tissue were determined by an enzyme-linked immunospot (ELISPOT) assay.

Bacterial aerosol challenge. The bacterial aerosol challenges were carried out one week after the last immunization in an inhalation exposure system (Glas-col, Terre Haute, Ind.) (Hu, W. G. et al. 1999 *Vaccine* 18:799-804). Conditions were as follows: challenge dose of bacteria, $10^8$ to $5 \times 10^8$ CFU/ml in the nebulizer; nebulizing time, 40 min; vacuum flowmeter, 60 standard $ft^3/h$; and compressed air flowmeter, 10 $ft^3/h$.

Measurement of bacterial clearance from mouse nasopharynx and lungs. At 6 h postchallenge, mice lungs were removed, and homogenated in 5 ml of PBS for 1 min at low speed in a tissue homogenizer (Stomacher Lab System Model 80, Seward, London, UK). At the same time, nasal washes were obtained by flushing the nasal cavity with 200 µl of PBS. The appropriately diluted or undiluted lung homogenates, and nasal washes were plated on chocolate agar plates, and the bacterial colonies were counted after overnight incubation. In addition, sera, nasal washes and lung homogenates were collected for antibody quantification.

Statistical analysis. The viable bacteria were expressed as the geometric mean CFU of n independent observations±standard deviation. Geometric means of reciprocal antibody titers were determined. Significance was determined by Student's t test.

Results

TABLE 4

Murine antibody responses against LOS of *M. catarrhalis* strain 25238 elicited by dLOS-CRM conjugate vaccine

| Immunization Group[a] | Antibody class | GM antibody ELISA titers[b] | | | | |
|---|---|---|---|---|---|---|
| | | Nasal wash | Lung lavage | Saliva | Fecal Extract | Serum |
| ① dLOS-CRM | IgA | 169 (36-782)**[c] | 144 (41-501)** | 30 (7-124)** | 21 (3-159)* | 48 (14-167)** |
| | IgG | 14 (6-31)** | 26 (8-83)** | 3 | 3 | 56 (8-412)** |
| | IgM | 3 | 3 | 3 | 3 | 48 (14-167)** |
| ② dLOS | IgA | 26 (13-53)** | 5 (2-13) | 5 (3-9) | 3 | 10 |
| | IgG | 3 | 3 | 3 | 3 | 10 |
| | IgM | 3 | 3 | 3 | 3 | 26 (18-39)** |
| ③ PBS | IgA | 3 | 3 | 3 | 3 | 10 |
| | IgG | 3 | 3 | 3 | 3 | 10 |
| | IgM | 3 | 3 | 3 | 3 | 10 |

[a]Mice were intranasally immunized 4 times at 1-week intervals with 10 µl of PBS containing a mixture of 5 µg of dLOS-CRM and 1 µg of CT, or 10 µl of PBS containing a mixture of 5 µg of dLOS and 1µ of CT, or 10 µl of PBS containing 1 µg of CT, respectively.
[b]Geometric mean (±SD range) of six to eight mice.
[c]Group 1, or group 2 versus group 3: *P < 0.05, **P < 0.01.

TABLE 5

Effect of intranasal immunization with dLOS-CRM on bacterial recovery of homologous strain 25238 in mouse nasopharynx and lungs[a]

| Immunogen | Nasopharynx | | Lung | |
|---|---|---|---|---|
| | Bacterial recovery[b] (CFU/lung) | Bacterial reduction[c] (%) | Bacterial recovery[b] (CFU/mouse) | Bacterial reduction[c] (%) |
| ① dLOS-CRM | 91 (41-201)[d] | 75 | 1290 (555-2998)[d] | 87 |
| ② dLOS | 354 (188-669) | 2 | 8872 (6468-12169) | 8 |
| ③ PBS | 362 (250-516) | 0 | 9656 (8130-11472) | 0 |

[a]See Table 4, footnote a. One week after the last immunization, mice were challenged with $2 \times 10^8$ CFU of *M.catarrhalis* strain 25238 per ml in a nebulizer, and nasal washes and lungs were collected at 6 h postchallenge, respectively.
[b]Geometric mean (±SD range) of six to eight mice.
[c]Compared with group 3.
[d]P < 0.01 compared with group 2 or group 3.

TABLE 6

Murine antibody responses against LOS of *M. cat* strain 25238 elicited by different dLOS-protein conjugates

| Immunization Group[a] | Antibody class | GM antibody ELISA titers[b] | | | | |
|---|---|---|---|---|---|---|
| | | Nasal wash | Lung lavage | Saliva | Fecal Extract | Serum |
| ① dLOS-CRM | IgA | 231 (61-877)**[c] | 105 (24-462)** | 12 (4-32)** | 5 (2-12) | 56 (24-133)** |
| | IgG | 16 (9-29)** | 26 (7-97)** | 4 (2-6) | 5 (3-10) | 123 (36-418)** |
| | IgM | 3 | 13 (6-32)** | 3 | 3 | 30 (12-74)** |
| ② dLOS | IgA | 103 (35-307)** | 52 (10-274)** | 5 (2-13) | 5 (2-11) | 34 (14-86)** |
| | IgG | 11 (4-31)** | 10 (3-32)* | 4 (2-9) | 4 (2-9) | 45 (20-103)** |
| | IgM | 3 | 7 (4-13)** | 3 | 3 | 20 (9-45)* |
| ③ dLOS-UspA | IgA | 26 (10-65)** | 17 (10-31)** | 4 (2-7) | 5 (2-11) | 17 (10-31)* |
| | IgG | 6 (3-15)** | 6 (3-12)** | 3 | 6 (2-24) | 20 (11-35)** |
| | IgM | 3 | 5 (3-10)* | 3 | 3 | 17 (10-31)* |
| ④ PBS | IgA | 3 | 3 | 3 | 3 | 10 |
| | IgG | 3 | 3 | 3 | 3 | 10 |
| | IgM | 3 | 3 | 3 | 3 | 10 |

[a]Mice were intranasally immunized 4 times at 1-week intervals with 10 μl of PBS containing a mixture of 5 μg of dLOS-CRM, dLOS-TT or dLOS-UspA and 1 μg of CT, or 10 μl of PBS containing 1 μg of CT, respectively.
[b]Geometric mean (±SD range) of eight mice.
[c]Group 1, 2, or 3 versus group 4: *$P < 0.05$; **$P < 0.01$.

TABLE 7

Murine antibody responses against LOS of *M. catarrhalis* strain 25238 elicited by dLOS-CRM conjugate through different immunization regimens

| Immunogen[a] | Immunization route | Antibody class | GM antibody ELISA titers[b] | | |
|---|---|---|---|---|---|
| | | | Nasal wash | Lung homogenate | Serum |
| ① dLOS-CRM | intranasal | IgA | 118 (26-545) | 111 (23-530) | 78 (18-348) |
| | | IgG | 20 (5-73) | 73 (13-396) | 156 (20-1192) |
| | | IgM | 3 | 31 (11-87) | 26 (13-53) |
| ② PBS | intranasal | IgA | 3**[c] | 3** | 10** |
| | | IgG | 3** | 3** | 10** |
| | | IgM | 3 | 3** | 10** |
| ③ dLOS-CRM | subcutaneous | IgA | 13 (8-22)** | 15 (7-31)** | 17 (8-40)* |
| | | IgG | 15 (9-27) | 161 (22-1185) | 536 (60-4805) |
| | | IgM | 3 | 31 (11-87) | 17 (8-40) |
| ④ PBS | subcutaneous | IgA | 3** | 3** | 10** |
| | | IgG | 3** | 3** | 10** |
| | | IgM | 3 | 3** | 10** |

[a]Mice were intranasally administered 4 times at 1-week intervals with 10 μl of PBS containing a mixture of 5 μg of dLOS-CRM and 1 μg of CT, or 10 μl of PBS containing 1 μg of CT, or subcutaneously injected 3 times at 2-week intervals with 0.2 ml of a mixture of 5 μg of dLOS-CRM and 1 μg of CT, or 0.2 ml of PBS containing 1 μg of CT, respectively.
[b]Geometric mean (±SD range) of eight mice.
[c]Group 2, 3, or 4 versus group 1: *$P < 0.05$; **$P < 0.01$.

Figure 8A:
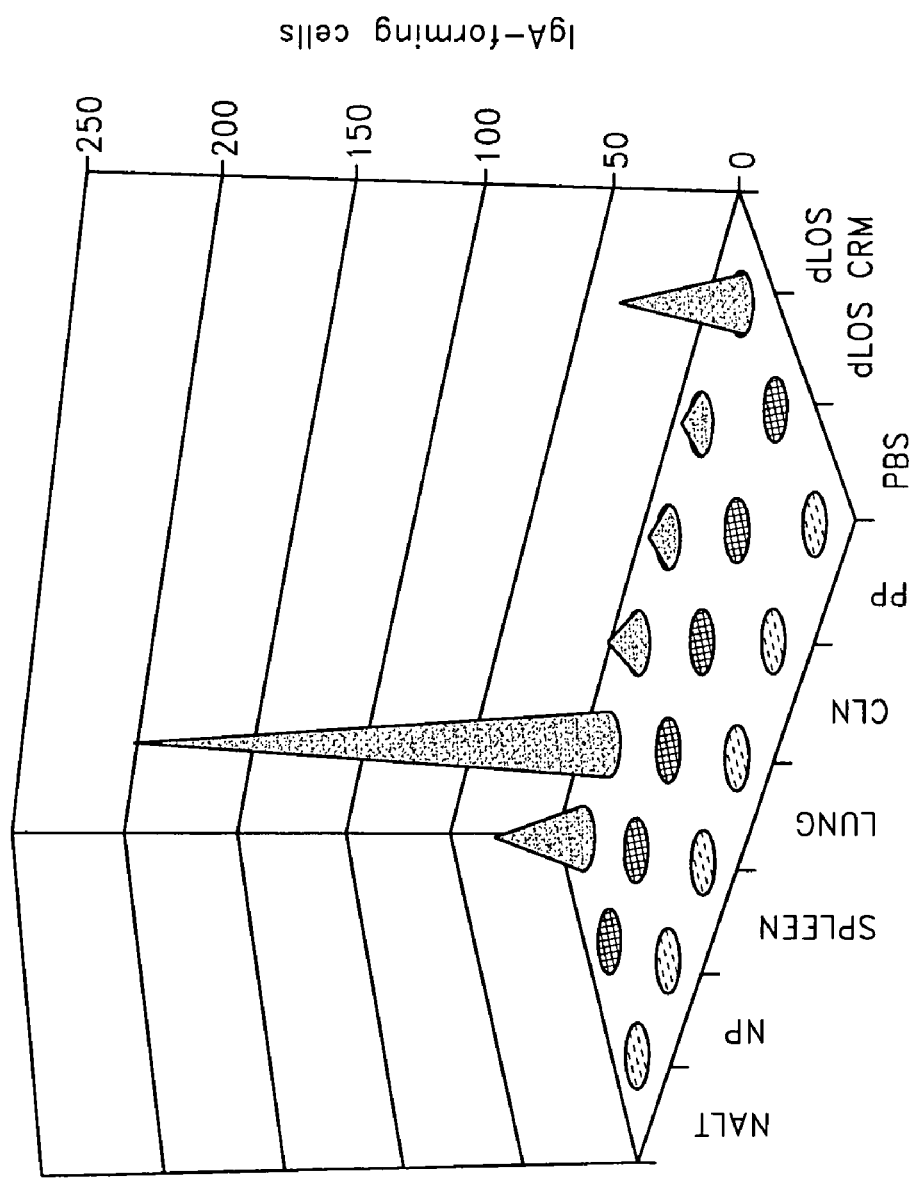
FIG. 8A-C. Specific antibody-forming cells induced by dLOS-CRM conjugate measured by ELISPOT assay. See Table 4, footnote a. (A) IgA-forming cells per million of lymphoid cells; (B) IgG-forming cells per million of lymphoid cells; (C) IgM-forming cells per million of lymphoid cells. NALT: nasal-associated lymphoid tissue, NP: nasal passage, CLN: cervical lymph node, PP: Peyer's patch.
Figure 8B:
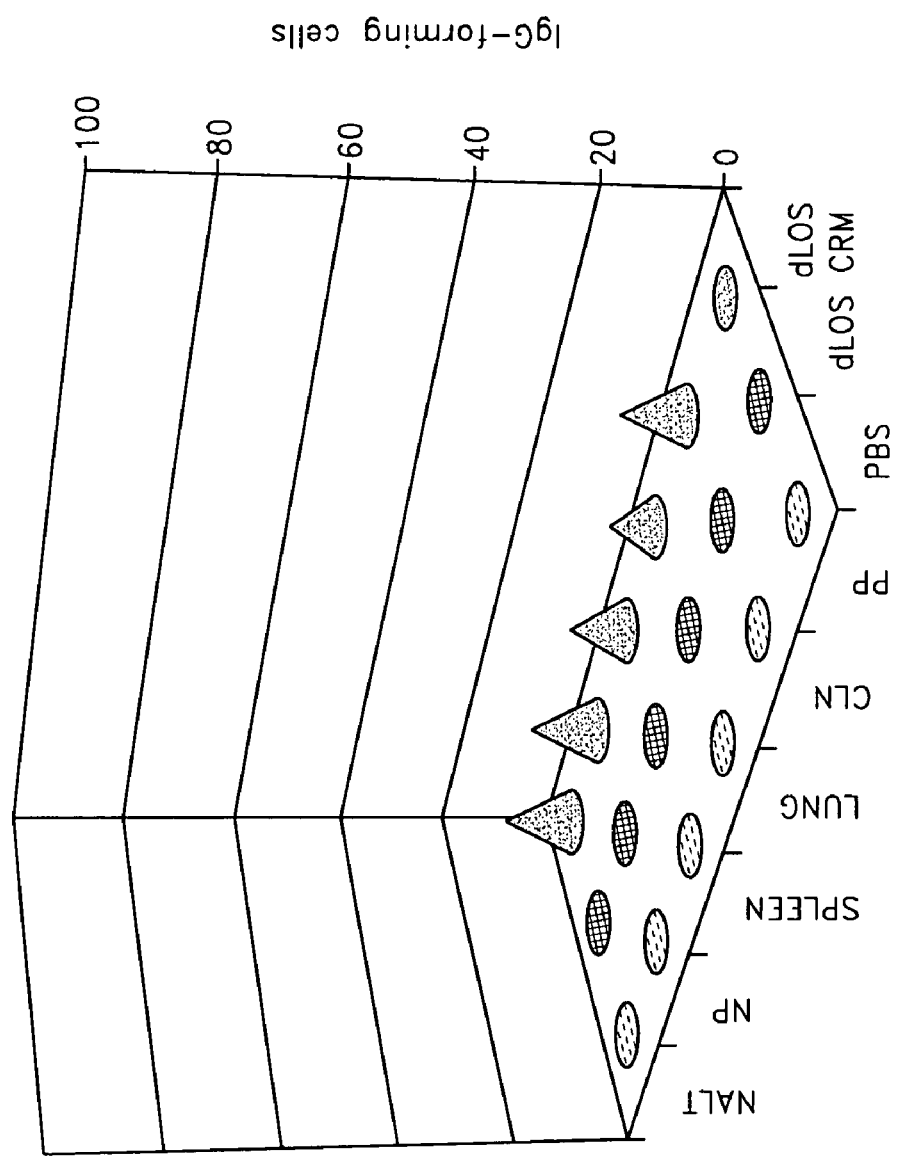
Figure 8C:
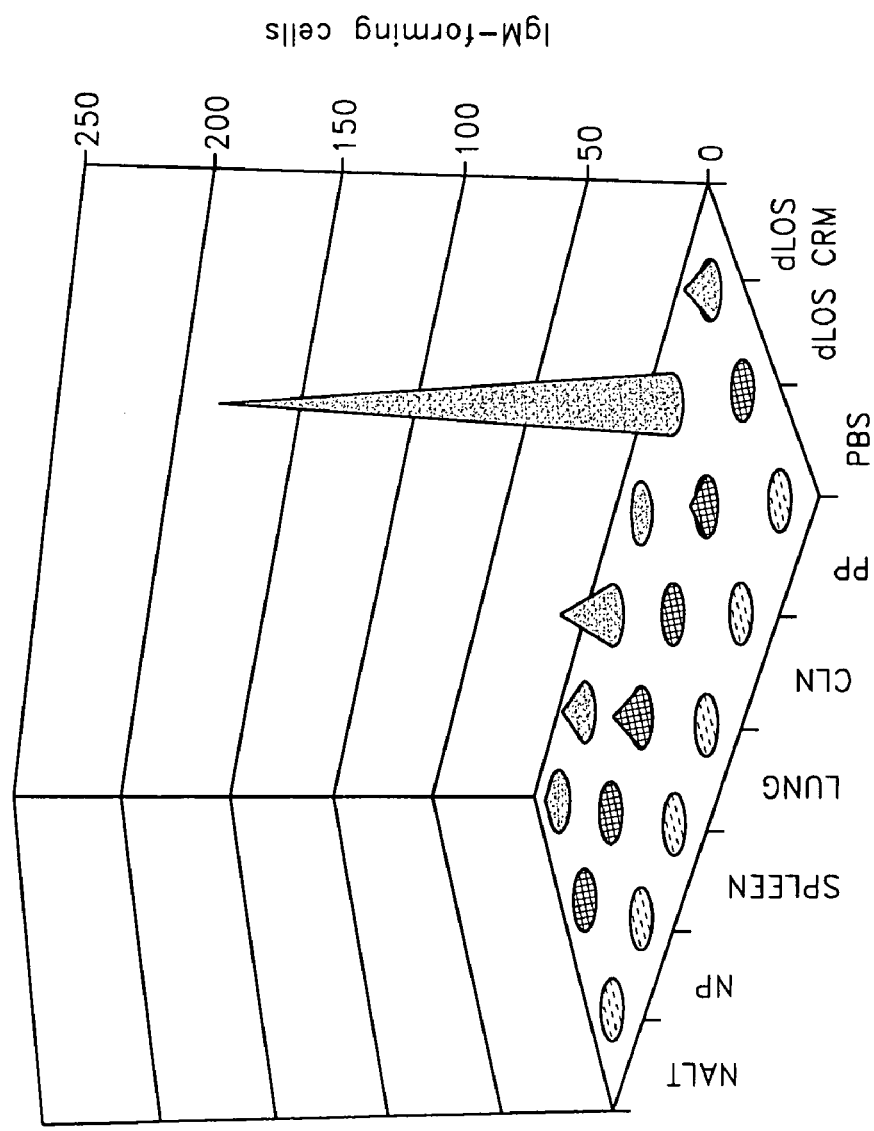
Figure 9A:
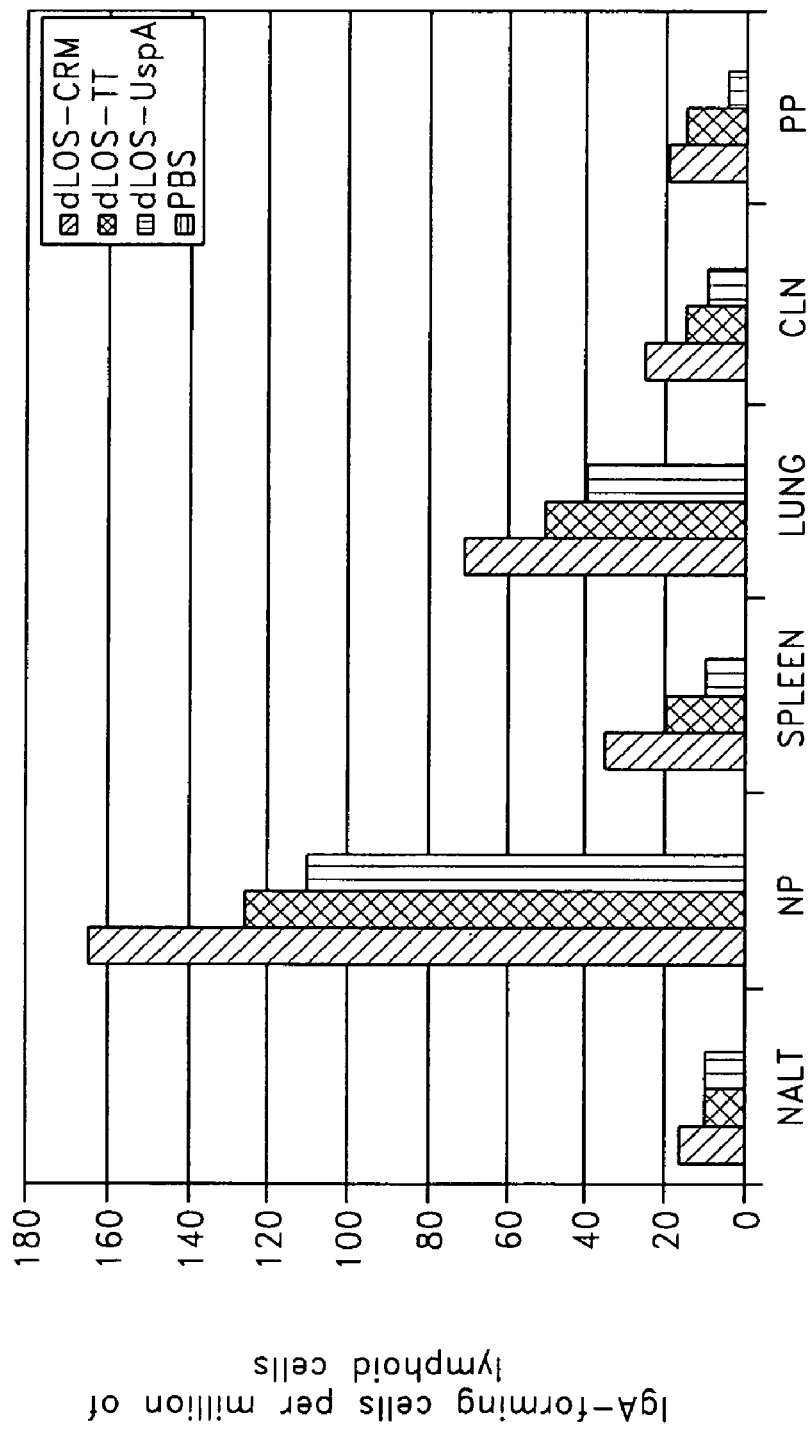
FIG. 9A-C. Specific antibody-forming cells initiated by different dLOS-protein conjugates. See Table 6, footnote a. NALT: nasal-associated lymphoid tissue, NP: nasal passage, CLN: cervical lymph node, PP: Peyer's patch.
Figure 9B:
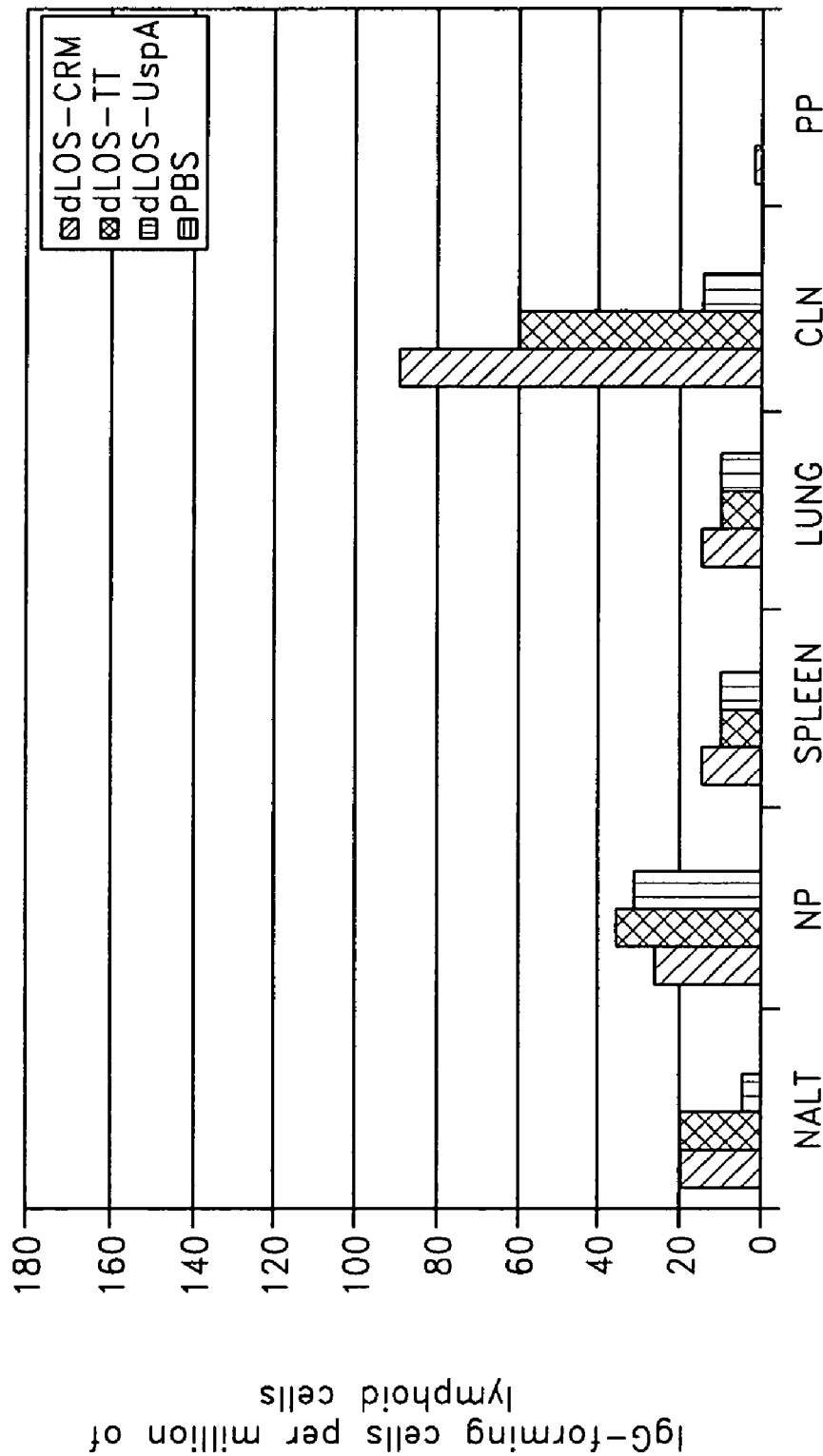
Figure 9C:
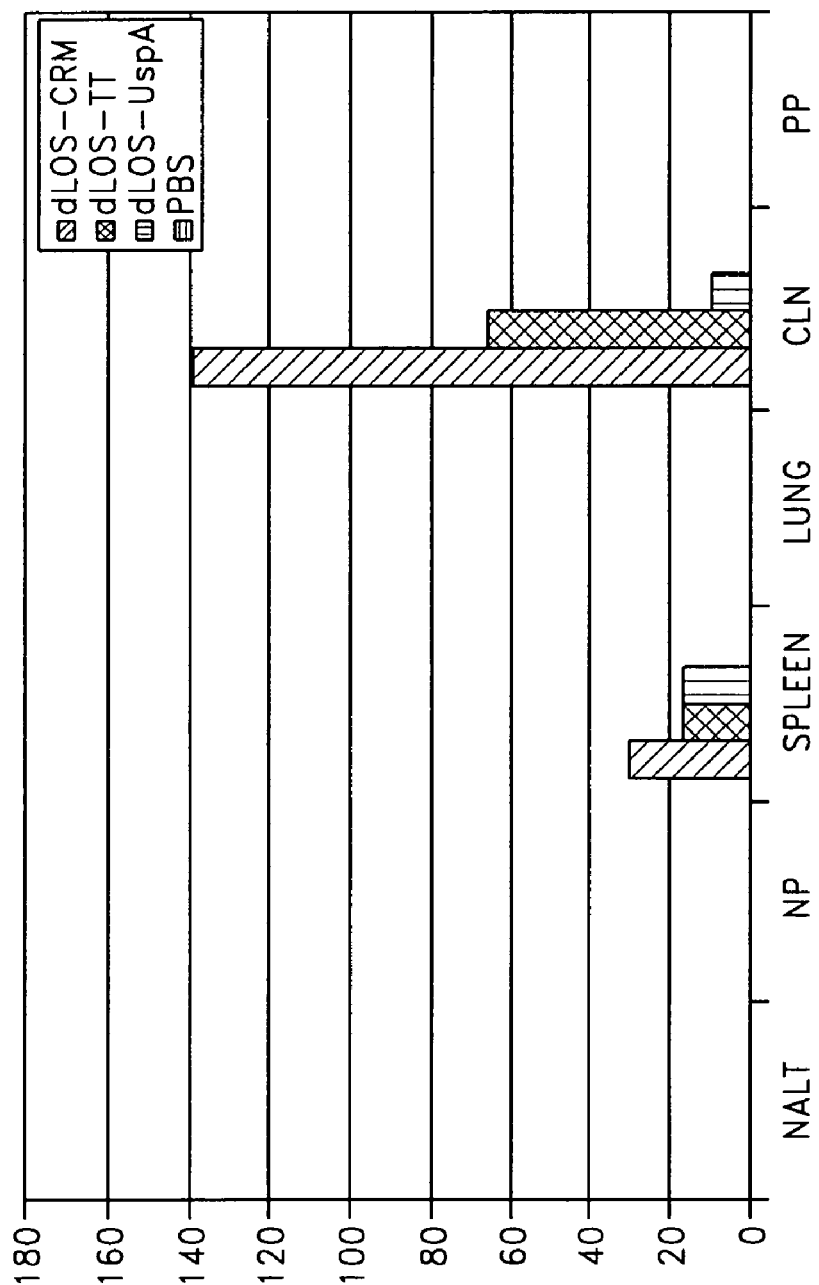
Figure 10A:
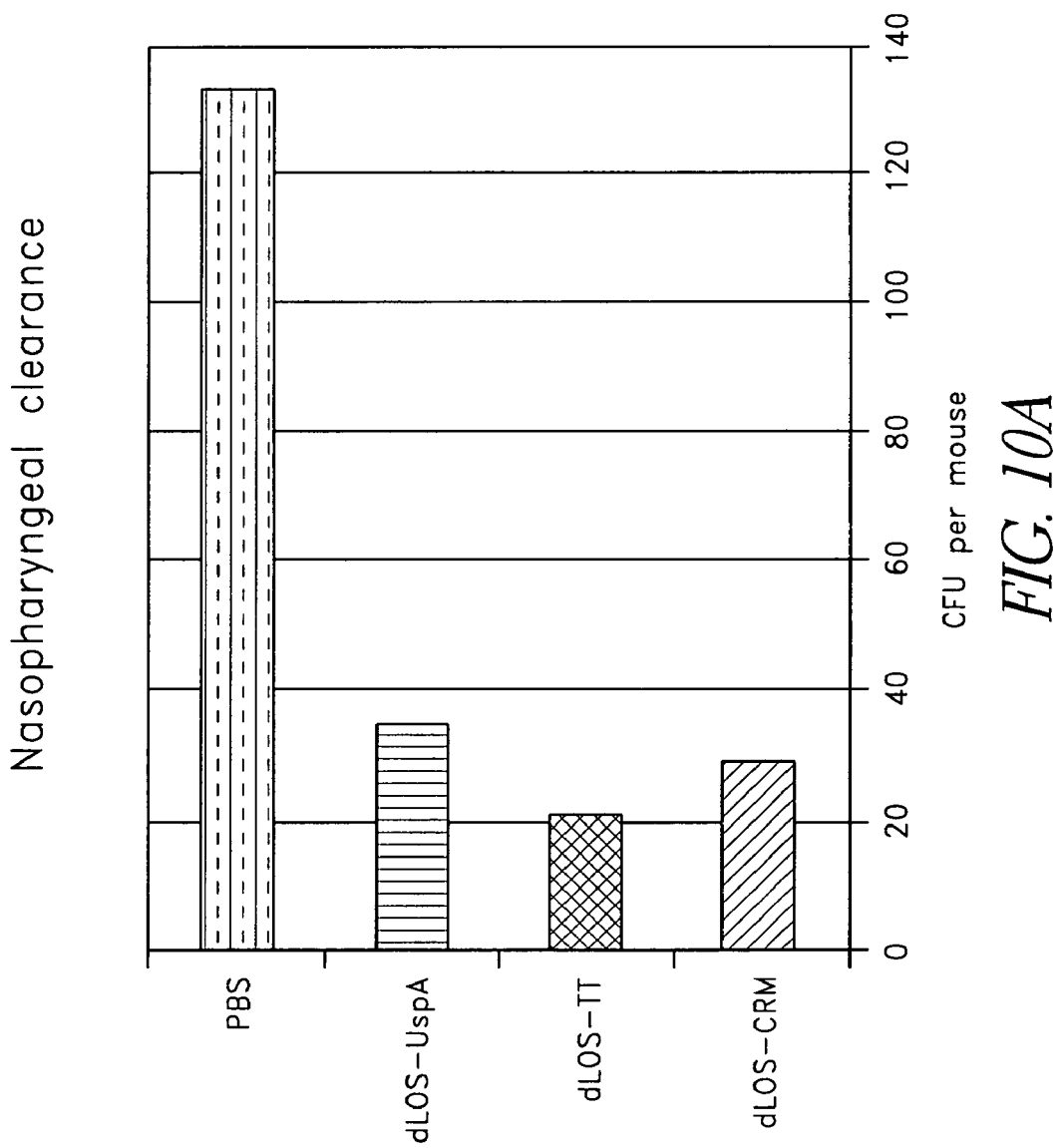
FIG. 10A-B. Comparison of protective effect induced by different dLOS-protein conjugates in bacterial clearance from mouse nasopharynx and lungs. See Table 6, footnote a. One week after the last immunization, mice were challenged with $2 \times 10^8$ CFU of *M. catarrhalis* strain 25238 per ml in a nebulizer, and nasal washes and lungs were collected at 6 h postchallenge. The CFU of bacterial recovery from CT group compared to that of other group: P<0.01.
Figure 10B:
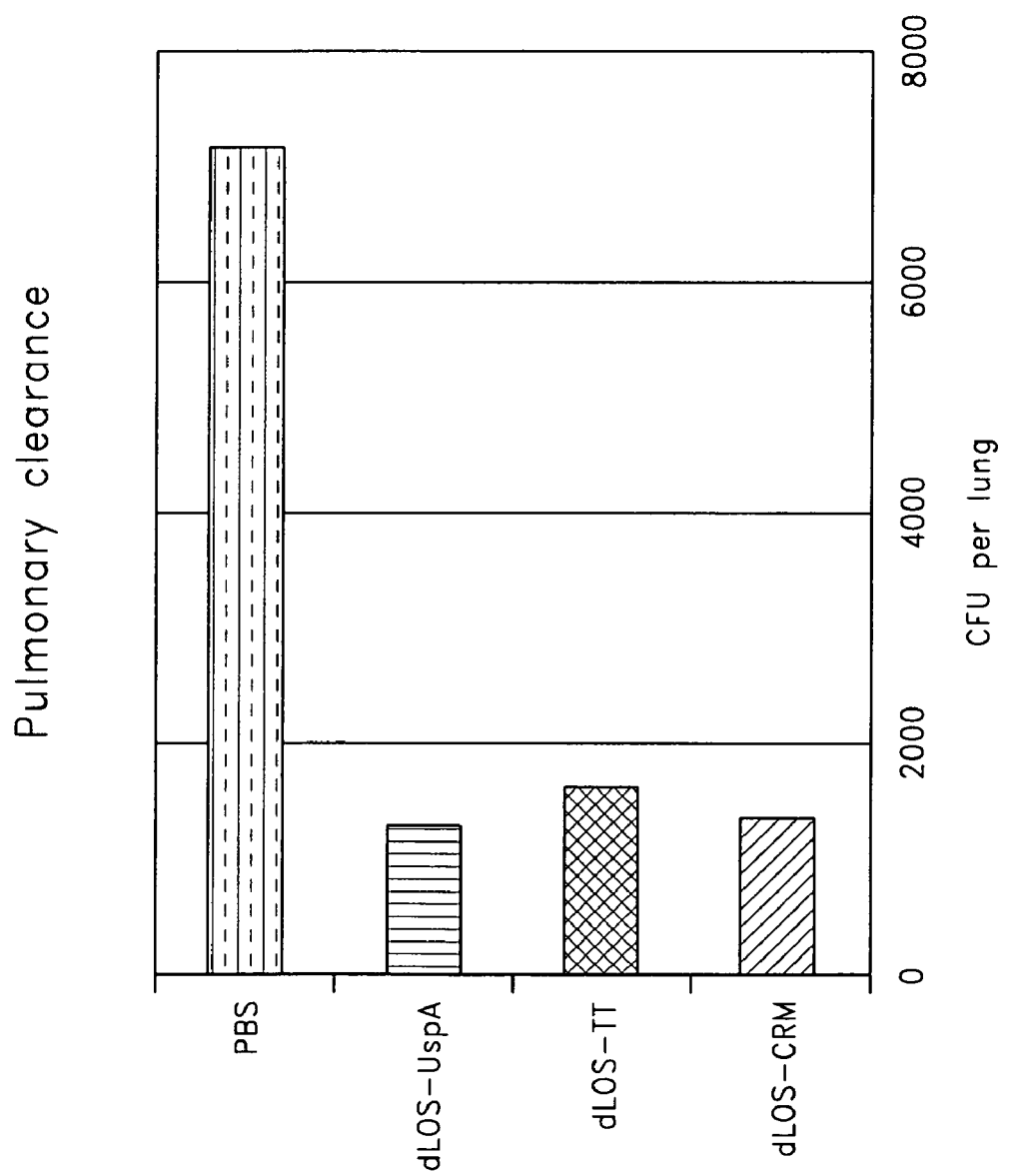
Figure 11:
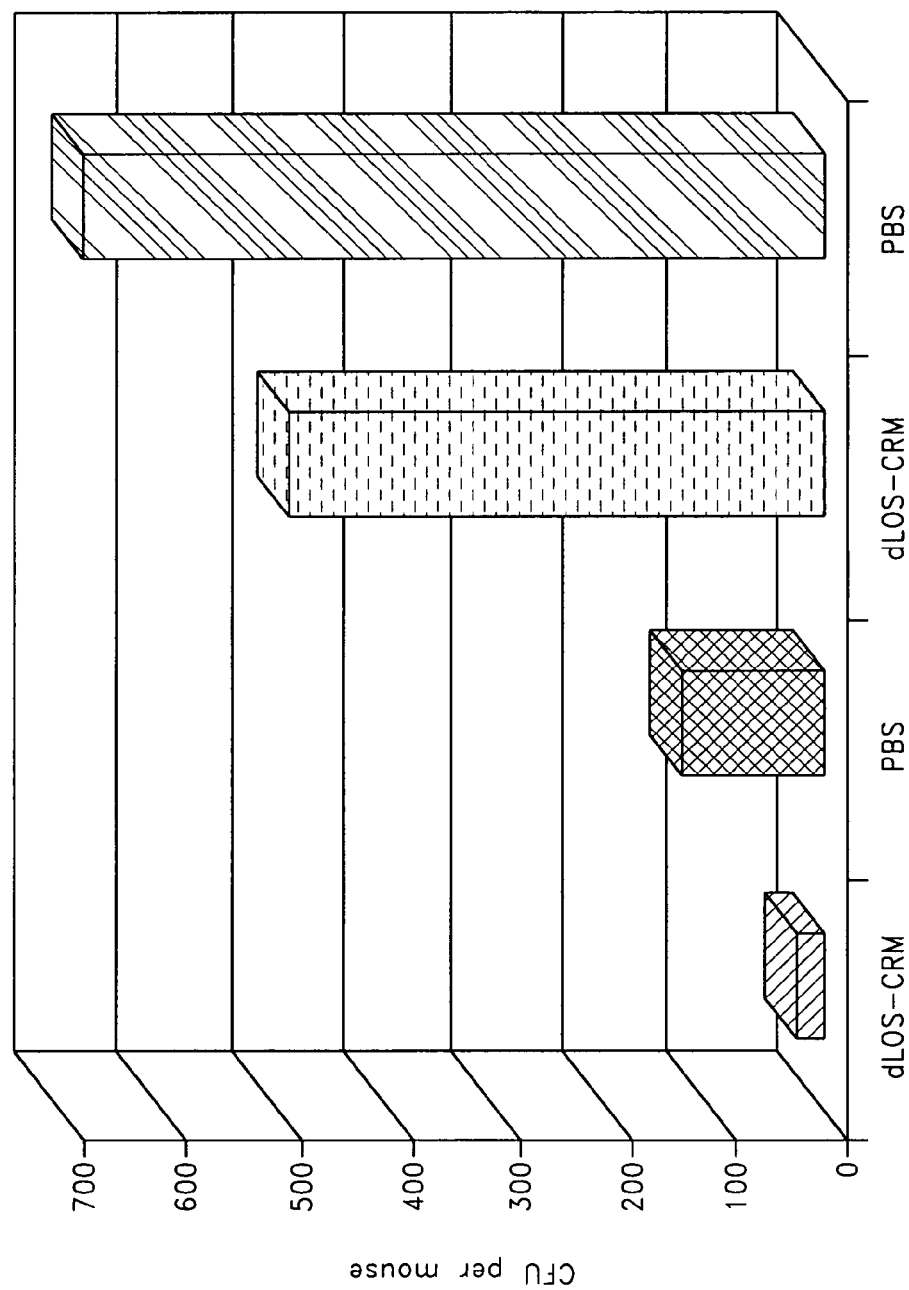
FIG. 11. Comparison of protective effect from different immunization regimens in bacterial clearance from mouse nasopharynx. See Table 7, footnote a. One week after the last immunization, mice were challenged with $2 \times 10^8$ CFU of *M. catarrhalis* strain 25238 per ml in a nebulizer, and nasal washes were collected at 6 h postchallenge. Left two bars: intranasal immunization, right two bars: subcutaneous injection.
Figure 12:
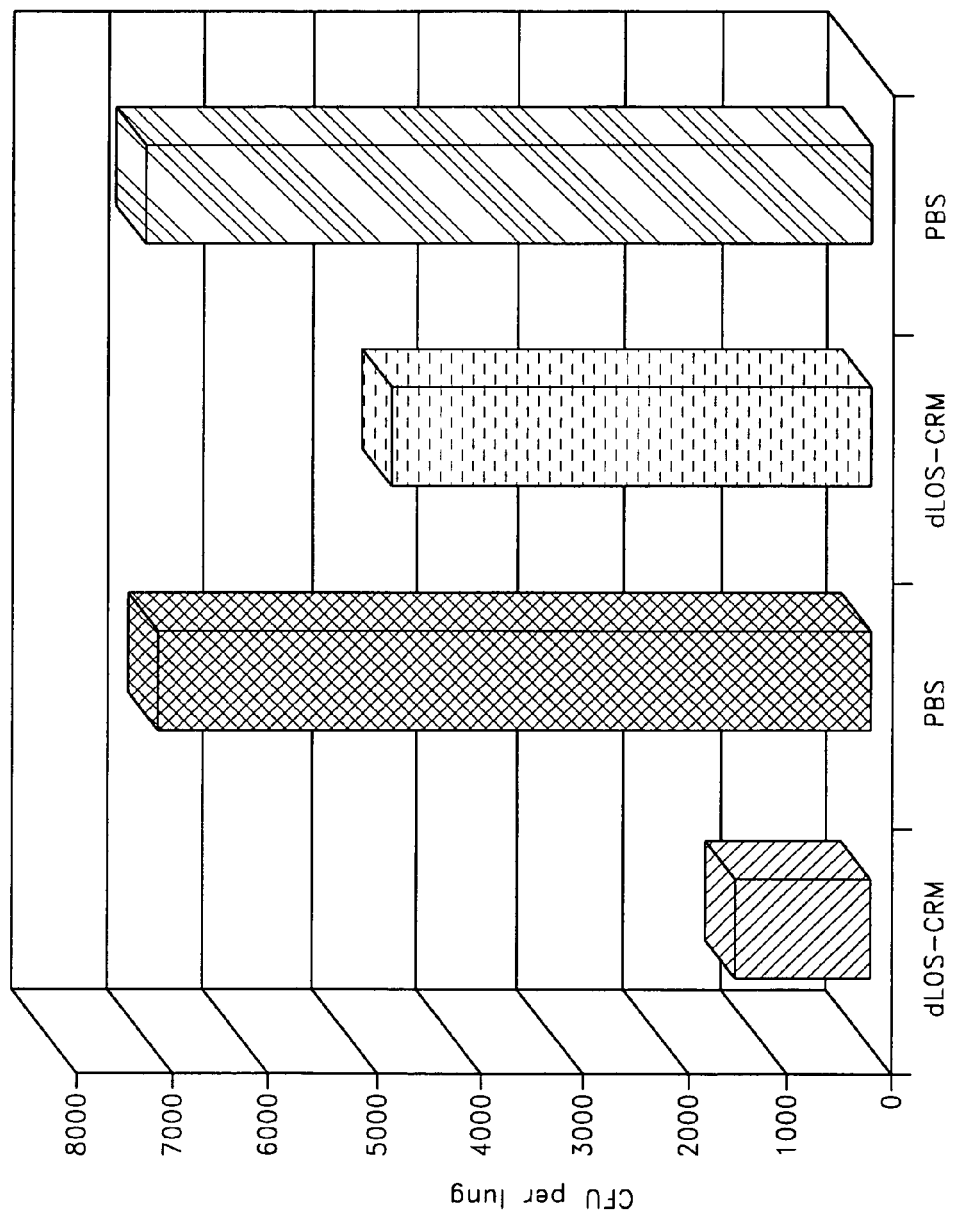
FIG. 12. Comparison of protective effect from different immunization regimens in bacterial clearance from mouse lungs. See Table 7, footnote a. One week after the last immunization, mice were challenged with $2 \times 10^8$ CFU of *M. catarrhalis* strain 25238 per ml in a nebulizer, and lungs were collected at 6 h postchallenge. Left two bars: intranasal immunization, right two bars: subcutaneous injection.
Figure 13:
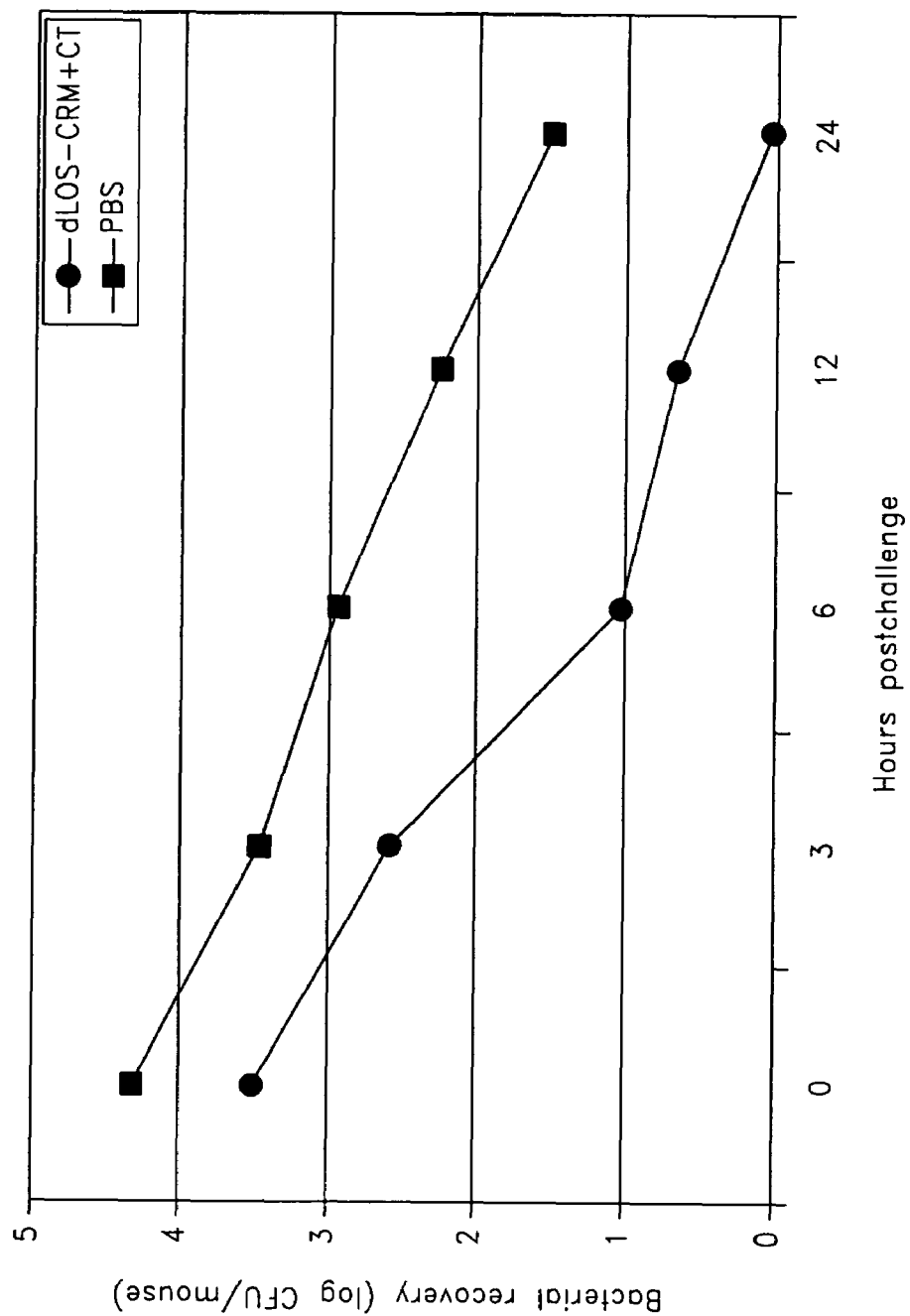
FIG. 13. Kinetics of bacterial recovery from mouse nasopharynx challenged with *M. catarrhalis* strain 25238. Mice were intranasally administered 4 times at 1-week intervals with 10 μl of PBS containing a mixture of 5 μg of dLOS-CRM and 1 μg of CT, or 10 μl of PBS. One week after the last immunization, mice were challenged with $5 \times 10^8$ CFU of *M. catarrhalis* strain 25238 per ml in a nebulizer, and nasal washes or lungs were collected at 0, 3, 6, 12, 24 h postchallenge, respectively. At each time point, immunized mice significantly reduced bacterial recovery from nasopharynx and lungs, and bacterial recovery became undetectable within 24 h, postchallenge.
Figure 14:
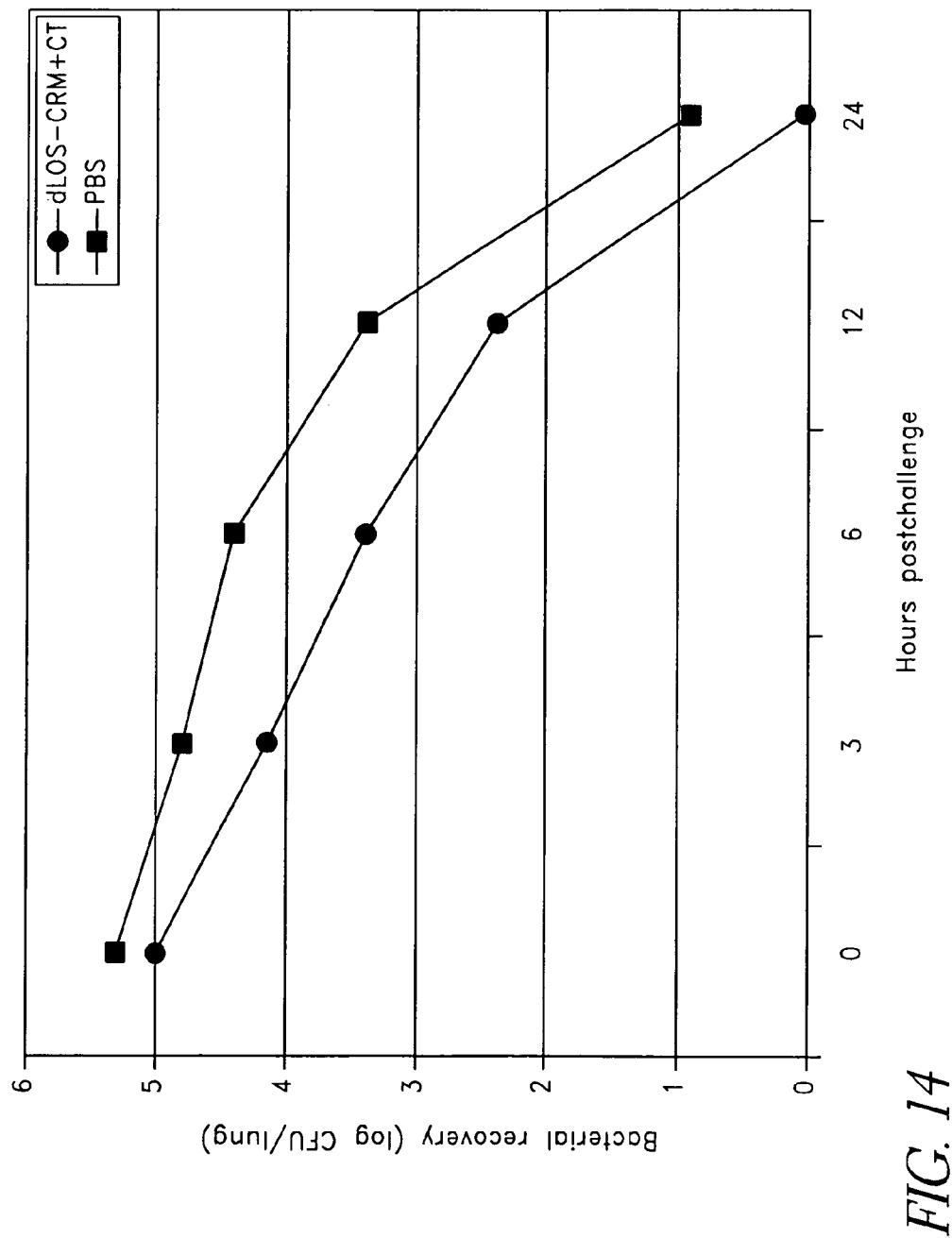
FIG. 14. Kinetics of bacterial recovery from mouse lungs challenged with *M. catarrhalis* strain 25238. See description of FIG. 13.

Conclusions. Intranasal immunization with dLOS-CRM induced both mucosal and systemic immunity (Table 4, FIG. 8A-C). Intranasal immunization with dLOS-CRM significantly enhanced *M. catarrhalis* clearance from mouse nasopharynx and lungs (Table 5). Different conjugate vaccines elicited similar protection against *M. catarrhalis* (Table 6, FIGS. 9A-C and 10A-B). Compared to subcutaneous injection, intranasal immunization with dLOS-CRM showed a higher level of bacterial clearance from mouse nasopharynx and lungs (Table 7, FIGS. 11 and 12). At each time point, immunized mice significantly reduced bacterial recovery from nasopharynx and lungs, and bacterial recovery became undetectable within 24 h postchallenge (FIGS. 13 and 14).

While the present invention has been described in some detail for purposes of clarity and understanding, one skilled in the art will appreciate that various changes in form and detail can be made without departing from the true scope of the invention. All references referred to above are hereby incorporated by reference.

What is claimed is:

1. A method for inducing an immunological response against NTHi or *M. catarrhalis* comprising intranasal administration of an immunogenic composition comprising an effective amount of Nontypeable *Haemophilus influenzae* (NTHi) lipooligosaccharide (LOS) or *Moraxella catarrhalis* lipooligosaccharide (LOS), said LOS produced by Nontypeable *Haemophilus influenzae* or *Moraxella catarrhalis*, from which LOS at least one primary O-linked fatty acid has been removed to form detoxified LOS (dLOS) and an immunogenic carrier covalently linked thereto, and a mucosal adjuvant or delivery system;

wherein said at least one primary O-linked fatty acid is removed by breaking the bond coupling said primary O-linked fatty acid to a 3-hydroxy group of diglucosamine; and wherein administration of said effective amount of NTHi LOS induces an immunological response against NTHi and administration of said effective amount of *M. catarrhalis* LOS induces an immunological response against *M. catarrhalis*.

2. The method of claim 1, wherein said mucosal adjuvant or delivery system comprises aluminum salts.

3. The method of claim 1, wherein said mucosal adjuvant or delivery system comprises chitosan.

4. The method of claim 1, wherein said mucosal adjuvant or delivery system comprises cytokines.

5. The method of claim 1, wherein said mucosal adjuvant or delivery system comprises saponins.

6. The method of claim 1, wherein said mucosal adjuvant or delivery system comprises muramyl dipeptide (MDP) derivatives.

7. The method of claim 1, wherein said mucosal adjuvant or delivery system comprises CpG oligos.

8. The method of claim 1, wherein said mucosal adjuvant or delivery system comprises lipopolysaccharide (LPS) of gram-negative bacteria.

9. The method of claim 1, wherein said mucosal adjuvant or delivery system comprises monophosphoryl lipid A (MPL).

10. The method of claim 1, wherein said mucosal adjuvant or delivery system comprises polyphosphazenes.

11. The method of claim 1, wherein said mucosal adjuvant or delivery system comprises emulsions.

12. The method of claim 1, wherein said mucosal adjuvant or delivery system comprises virosomes.

13. The method of claim 1, wherein said mucosal adjuvant or delivery system comprises immune stimulating complexes (ISCOMs).

14. The method of claim 1, wherein said mucosal adjuvant or delivery system comprises cochleates.

15. The method of claim 1, wherein said mucosal adjuvant or delivery system comprises poly(lactide-co-glycolides) (PLG) microparticles.

16. The method of claim 1, wherein said mucosal adjuvant or delivery system comprises poloxamer particles.

17. The method of claim 1, wherein said mucosal adjuvant or delivery system comprises virus-like particles.

18. The method of claim 1, wherein said mucosal adjuvant or delivery system comprises heat-labile enterotoxin (LT) B subunit.

19. The method of claim 1, wherein said mucosal adjuvant or delivery system comprises cholera toxin (CT) B subunit.

20. The method of claim 1, wherein said mucosal adjuvant or delivery system comprises a non-toxic form of a toxin.

21. The method of claim 1, wherein said mucosal adjuvant or delivery system comprises microparticles.

22. The method of claim 1, wherein said mucosal adjuvant or delivery system comprises liposomes.

23. The method of claim 1, wherein said dLOS and said immunogenic carrier are covalently linked by a linker.

24. The method of claim 1, wherein said dLOS is detoxified lipooligosaccharide from Nontypeable *Haemophilus influenzae*.

25. The method of claim 1, wherein said dLOS is detoxified lipooligosaccharide from *Moraxella catarrhalis*.

* * * * *